United States Patent
Patel et al.

(10) Patent No.: US 6,649,387 B2
(45) Date of Patent: Nov. 18, 2003

(54) ENZYMATIC OXIDATIVE DEAMINATION PROCESS

(75) Inventors: Ramesh N. Patel, Bridgewater, NJ (US); Amit Banerjee, St. Louis, MO (US); Venkata B. Nanduri, East Brunswick, NJ (US); Steven L. Goldberg, Basking Ridge, NJ (US); Robert M. Johnston, Whitehouse Station, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 112 days.

(21) Appl. No.: 09/842,987

(22) Filed: Apr. 26, 2001

(65) Prior Publication Data

US 2002/0025566 A1 Feb. 28, 2002

Related U.S. Application Data

(62) Division of application No. 09/386,588, filed on Aug. 31, 1999, now Pat. No. 6,261,810.
(60) Provisional application No. 60/098,956, filed on Sep. 3, 1998.

(51) Int. Cl.$^7$ ............................ C12N 9/10; C12N 1/14; C12N 15/00; C12P 27/06; C07H 21/04
(52) U.S. Cl. ................ 435/193; 435/252.3; 435/320.1; 435/69.1; 435/252.33; 435/254.1; 536/23.2
(58) Field of Search ............................ 536/23.2, 23.1; 435/193, 320.1, 252.3, 252.33, 254.11, 440, 325

(56) References Cited

U.S. PATENT DOCUMENTS 5,508,272 A     4/1996   Robl
6,261,810 B1 *  7/2001   Patel et al. ................. 435/119

FOREIGN PATENT DOCUMENTS

EP        0 036 776      11/1988

OTHER PUBLICATIONS

Hames et al., Nucleic Acid Hybridization, A Practical Approach, IRL Press, Washington, D.C. (1985), Title and publication pages, and pp. 113–137 (Chapter 5).
Kern, B. et al., Antimicrobial Agents and Chemotherapy, American Society of Microbiology, vol. 17, No. 4, pp. 679–685 (1986).
Madduri, K. et al., Journal of Bacteriology, vol. 173, No. 3, pp. 985–988 (1991).
Coque, J. et al., Journal of Bacteriology, vol. 173, No. 19, pp. 6258–6264 (1991).
Houghton et al., Proc.Natl Acad.Sci. 82, 5131–5135 (1985).
Devereux et al., Nucl.Acids Res. 12:387–395 (1984).
Needleman et al., J. Mol. Biol. 48:443–453 (1970).
Smith et al., Adv.Appl.Math 2:482 (1981).
Gribskov et al., Nucl. Acids Res. 14:6745–6763 (1986).
Schwartz et al., Atlas of Protein Sequence and Structure, National Biomedical Research Foundation, 353–358 (1979).
White et al., Trends Genet. 5:185–189 (1989).
Morinaga et al., Nucl. Acids Res. 2:636–639 (1984).
Taylor et al., Nucl, Acids Res. 13: 8746–8764 (1985).
Kunkel, Proc. Natl. Acad. Sci USA 82:482–492 (1985).
Sayers et al., Nucl. Acids Res. 16:791–802 (1988).
Takada et al., J. Biochem. 109:371–376 (1991).
Bolivar et al., Gene 2:95–113 (1977).
Chang et al., Nature, 275:617–624 (1978).
Goeddel et al., Nature 281:544–548 (1979).
Goeddel et al., Nucl. Acids Res. 8:4057–4074 (1980).
Amann et al., Gene 25, 167–178 (1983).
Siebenlist et al., Cell 20:269–281 (1980).
Sanger et al., Proc.Natl.Acad.Sci.USA 74:5463–5467 (1977).
Maxam et al., Proc.Natl.Acad.Sci.USA 74:560–564 (1977).
Park et al. J. Bacteriol 1997, vol. 179, No. 17, pp. 5300–5308.
Oku et al. Biosci. Biotech.Biochem. 1998, vol. 62, No. 4, pp. 622–627.

* cited by examiner

Primary Examiner—Rebecca E. Prouty
Assistant Examiner—Malgorzata A Walicka
(74) Attorney, Agent, or Firm—Audrey P. Sher

(57) ABSTRACT

The present invention concerns an enzymatic oxidative deamination process of a dipeptide monomer to prepare an intermediate useful to prepare compounds having endopeptidase and angiotensin converting enzyme inhibition activity.

29 Claims, 1 Drawing Sheet

```
368/1                                           398/11
ATG TCG ATT ACG CCG CTC ATG CCC GTT TAC CCC CGG TGC GAT GTG CGT CCG GTC CGA GGC
Met ser ile thr pro leu met pro val tyr pro arg cys asp val arg pro val arg gly
428/21                                          458/31
GAG GGC TGC TAC CTG ATC GGG GAG CGC GGC GAG CGC TAT CTC GAC TTC GCC AGC GGT ATC
glu gly cys tyr leu ile gly glu arg gly glu arg tyr leu asp phe ala ser gly ile
488/41                                          518/51
GCC GTC AAT CTG CTG GGC CAT GGC CAC CCC AAG CTG GTG AAG ACC ATT GCC GAT CAG GCT
ala val asn leu leu gly his gly his pro lys leu val lys thr ile ala asp gln ala
548/61                                          578/71
GCG ACG CTG ATG CAT ATC TCC AAC CTC TAC GGC TCG CCG CTG GGG GAG GAA TTT GCG CAG
ala thr leu met his ile ser asn leu tyr gly ser pro leu gly glu glu phe ala gln
608/81                                          638/91
AAG CTG GTC GAT AAC AGT TTC GCG GAC ACC GTT TTC TTC ACC AAT TCG GGT GCC GAA GCG
lys leu val asp asn ser phe ala asp thr val phe phe thr asn ser gly ala glu ala
668/101                                         698/111
GTC GAG TGC GCG ATC AAG ACC GCG CGC CGC TAT CAT TAT GCC AAT GGG CAA GCG CAC CGG
val glu cys ala ile lys thr ala arg arg tyr his tyr ala asn gly gln ala his arg
728/121                                         758/131
CAC AAG ATC ATC AGC TTC GAC AAC GCC TTC CAC GGC CGC ACG CTG GGC ACC ATT TCG GCG
his lys ile ile ser phe asp asn ala phe his gly arg thr leu gly thr ile ser ala
788/141                                         818/151
ACC AGC CAG CCC AAG ATG CGC GAC GGG TTC GAG CCG CTG CTG CCC GGT TTC CAG GTC GTG
thr ser gln pro lys met arg asp gly phe glu pro leu leu pro gly phe gln val val
848/161                                         878/171
CCC TTC AAC GAT CTC GAC GCG GCG CTG GCC GCG ATC GAC GAC AAT ACC GCC GGT TTC CTG
pro phe asn asp leu asp ala ala leu ala ala ile asp asp asn thr ala gly phe leu
908/181                                         938/191
CTG GAA CCG GTG CAG GGT GAA GGC GGC GTG ACC CCG GCA ACC CAG GCA TTC CTG GCC GGC
leu glu pro val gln gly glu gly gly val thr pro ala thr gln ala phe leu ala gly
968/201                                         998/211
CTG CGC AAG GCG TGC GAC GAG CAG GGC CTG CTG CTG ATC CTG GAC GAG GTG CAG TGC GGC
leu arg lys ala cys asp glu gln gly leu leu leu ile leu asp glu val gln cys gly
1028/221                                        1058/231
TAT GCC CGT ACC GGC ACC TTC TTC GCC CAT GAA CAA TAT GGC GTG ACG CCG GAC ATC ATG
tyr ala arg thr gly thr phe phe ala his glu gln tyr gly val thr pro asp ile met
1088/241                                        1118/251
GCG GTG GCC AAG GGC ATC GGC GCG GGC TTC CCG CTC GGC GCC TGC CTC GCT ACC GAG GAT
ala val ala lys gly ile gly ala gly phe pro leu gly ala cys leu ala thr glu asp
1148/261                                        1178/271
GCG GCC AAG GGC ATG GTG TTC GGC ACC CAT GGT TCC ACC TAT GGC GGC AAC CCG CTC GCC
ala ala lys gly met val phe gly thr his gly ser thr tyr gly gly asn pro leu ala
1208/281                                        1238/291
ATG GCG GTG GGC ATC GCG GTG CTG GAA GAG GTG CTG GCG GAC GGG TTC CTG GAG CAG GTA
met ala val gly ile ala val leu glu glu val leu ala asp gly phe leu glu gln val
1268/301                                        1298/311
ACG CAT GGG TGC CGT CTG CGC TCT GCG CTG GAG CAG ATG ATC CCG AAC CAT GAC GAC ATG
thr his gly cys arg leu arg ser ala leu glu gln met ile pro asn his asp asp met
1328/321                                        1358/331
TTC GAG GAT GTG CGC GGC ATG GGG CTG ATG CTG GGC GTC AAG ATG AAG GAC GCC TAT GAC
phe glu asp val arg gly met gly leu met leu gly val lys met lys asp ala tyr asp
1388/341                                        1418/351
GCG CGT GCC TTT GTC GGC CAT CTG CGC GAC CAA CAT GGG TTC CTG TCG GTA TCG GCG GGC
ala arg ala phe val gly his leu arg asp gln his gly phe leu ser val ser ala gly
1448/361                                        1478/371
CAG AAT GTG CTG CGC ATC CTG CCG CCG CTC GTC ATC GAC GAA AGC CAT ATC GCC GAG TGC
gln asn val leu arg ile leu pro pro leu val ile asp glu ser his ile ala glu cys
1508/381                                        1538/391
ATC GAG AAG ATT TCC GCC GGC GCG CGG AGC TTC GCG GAC GCC AAG GCG GCC TGA
ile glu lys ile ser ala gly ala arg ser phe ala asp ala lys ala ala OPA
```

FIG. 1

SEQUENCE LISTING

<160> NUMBER OF SEQ ID NOS: 6

<210> SEQ ID NO 1
<211> LENGTH: 1191
<212> TYPE: DNA
<213> ORGANISM: Spingomonas paucimobilis

<400> SEQUENCE: 1

```
atgtcgatta cgccgctcat gcccgtttac ccccggtgcg atgtgcgtcc ggtccgaggc      60
gagggctgct acctgatcgg ggagcgcggc gagcgctatc tcgacttcgc cagcggtatc     120
gccgtcaatc tgctgggcca tggccacccc aagctggtga agaccattgc cgatcaggct     180
gcgacgctga tgcatatctc caacctctac ggctcgccgc tgggggagga atttgcgcag     240
aagctggtcg ataacagttt cgcggacacc gttttcttca ccaattcggg tgccgaagcg     300
gtcgagtgcg cgatcaagac cgcgcgccgc tatcattatg ccaatgggca agcgcaccgg     360
cacaagatca tcagcttcga caacgccttc cacggccgca cgctgggcac catttcggcg     420
accagccagc ccaagatgcg cgacgggttc gagccgctgc tgcccggttt ccaggtcgtg     480
cccttcaacg atctcgacgc ggcgctggcc gcgatcgacg acaataccgc cggtttcctg     540
ctggaaccgg tgcagggtga aggcggcgtg accccggcaa cccaggcatt cctggccggc     600
ctgcgcaagg cgtgcgacga gcagggcctg ctgctgatcc tggacgaggt gcagtgcggc     660
tatgcccgta ccggcaccct cttcgcccat gaacaatatg gcgtgacgcc ggacatcatg     720
gcggtggcca agggcatcgg cgcgggcttc ccgctcggcg cctgcctcgc taccgaggat     780
gcggccaagg gcatggtgtt cggcacccat ggttccacct atggcggcaa cccgctcgcc     840 atgcggtgg gcatcgcggt gctggaagag gtgctggcgg acgggttcct ggagcaggta     900
acgcatgggt gccgtctgcg ctctgcgctg gagcagatga tcccgaacca tgacgacatg     960
ttcgaggatg tgcgcggcat ggggctgatg ctggcgtca agatgaagga cgcctatgac    1020
gcgcgtgcct tgtcggcca tctgcgcgac caacatgggt tcctgtcggt atcggcgggc    1080
cagaatgtgc tgcgcatcct gccgccgctc gtcatcgacg aaagccatat cgccgagtgc    1140
```

```
atcgagaaga tttccgccgg cgcgcggagc ttcgcggacg ccaaggcggc c          1191
```

<210> SEQ ID NO 2
<211> LENGTH: 397
<212> TYPE: PRT
<213> ORGANISM: Spingomonas paucimobilis

<400> SEQUENCE: 2

```
Met Ser Ile Thr Pro Leu Met Pro Val Tyr Pro Arg Cys Asp Val Arg
 1               5                  10                  15

Pro Val Arg Gly Glu Gly Cys Tyr Leu Ile Gly Glu Arg Gly Glu Arg
            20                  25                  30

Tyr Leu Asp Phe Ala Ser Gly Ile Ala Val Asn Leu Leu Gly His Gly
        35                  40                  45

His Pro Lys Leu Val Lys Thr Ile Ala Asp Gln Ala Ala Thr Leu Met
50                  55                  60

His Ile Ser Asn Leu Tyr Gly Ser Pro Leu Gly Glu Phe Ala Gln
65                  70                  75                  80

Lys Leu Val Asp Asn Ser Phe Ala Asp Thr Val Phe Thr Asn Ser
                85                  90                  95

Gly Ala Glu Ala Val Glu Cys Ala Ile Lys Thr Ala Arg Arg Tyr His
            100                 105                 110

Tyr Ala Asn Gly Gln Ala His Arg His Lys Ile Ile Ser Phe Asp Asn
        115                 120                 125

Ala Phe His Gly Arg Thr Leu Gly Thr Ile Ser Ala Thr Ser Gln Pro
    130                 135                 140

Lys Met Arg Asp Gly Phe Glu Pro Leu Leu Pro Gly Phe Gln Val Val
145                 150                 155                 160

Pro Phe Asn Asp Leu Asp Ala Ala Leu Ala Ala Ile Asp Asp Asn Thr
                165                 170                 175

Ala Gly Phe Leu Leu Glu Pro Val Gln Gly Glu Gly Gly Val Thr Pro
            180                 185                 190

Ala Thr Gln Ala Phe Leu Ala Gly Leu Arg Lys Ala Cys Asp Glu Gln
        195                 200                 205

Gly Leu Leu Leu Ile Leu Asp Glu Val Gln Cys Gly Tyr Ala Arg Thr
    210                 215                 220

Gly Thr Phe Phe Ala His Glu Gln Tyr Gly Val Thr Pro Asp Ile Met
225                 230                 235                 240

Ala Val Ala Lys Gly Ile Gly Ala Gly Phe Pro Leu Gly Ala Cys Leu
                245                 250                 255

Ala Thr Glu Asp Ala Ala Lys Gly Met Val Phe Gly Thr His Gly Ser
            260                 265                 270

Thr Tyr Gly Gly Asn Pro Leu Ala Met Ala Val Gly Ile Ala Val Leu
        275                 280                 285

Glu Glu Val Leu Ala Asp Gly Phe Leu Glu Gln Val Thr His Gly Cys
    290                 295                 300

Arg Leu Arg Ser Ala Leu Glu Gln Met Ile Pro Asn His Asp Asp Met
305                 310                 315                 320

Phe Glu Asp Val Arg Gly Met Gly Leu Met Leu Gly Val Lys Met Lys
                325                 330                 335

Asp Ala Tyr Asp Ala Arg Ala Phe Val Gly His Leu Arg Asp Gln His
            340                 345                 350

Gly Phe Leu Ser Val Ser Ala Gly Gln Asn Val Leu Arg Ile Leu Pro
        355                 360                 365
```

```
Pro Leu Val Ile Asp Glu Ser His Ile Ala Glu Cys Ile Glu Lys Ile
    370                 375                 380

Ser Ala Gly Ala Arg Ser Phe Ala Asp Ala Lys Ala Ala
385                 390                 395

<210> SEQ ID NO 3
<211> LENGTH: 24
<212> TYPE: DNA
<213> ORGANISM: Spingomonas paucimobilis

<400> SEQUENCE: 3
atyacsccgy tgatgccggt stat                                           24

<210> SEQ ID NO 4
<211> LENGTH: 8
<212> TYPE: PRT
<213> ORGANISM: Spingomonas paucimobilis

<400> SEQUENCE: 4

Ile Thr Pro Leu Met Pro Val Tyr
1               5

<210> SEQ ID NO 5
<211> LENGTH: 6
<212> TYPE: PRT
<213> ORGANISM: Spingomonas paucimobilis

<400> SEQUENCE: 5

Tyr Gly Asn Pro Leu Ala
1               5

<210> SEQ ID NO 6
<211> LENGTH: 17
<212> TYPE: DNA
<213> ORGANISM: Unknown
<220> FEATURE:
<223> OTHER INFORMATION: Conserved amino acid sequence found in other
      amino transferases

<400> SEQUENCE: 6
gcsagsgggt tsccscc                                                   17
```

ENZYMATIC OXIDATIVE DEAMINATION PROCESS

This application is a divisional of U.S. Ser. No. 09/386,588 filed Aug. 31, 1999, issued as U.S. Pat. No. 6,261,810, which claims priority from provisional application U.S. Serial No. 60/098,956 filed Sep. 3, 1998, both of which are incorporated herein by reference in their entirety.

FIELD OF INVENTION

The present invention concerns an enzymatic oxidative deamination process to prepare an intermediate useful to prepare compounds having endopeptidase and angiotensin converting enzyme inhibition activity.

BACKGROUND OF THE INVENTION

Robl in U.S. Pat. No. 5,508,272 discloses compounds of the formula

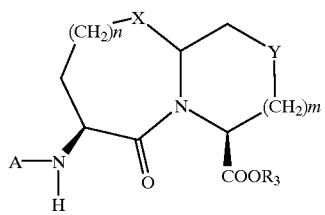

wherein A is

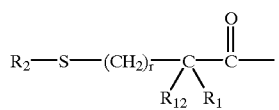

as possessing neutral endopeptidase and angiotensin converting enzyme inhibition activity. Among these compounds is [4S-[4α(R*),7α,10aβ]]-octahydro-4-[(2-mercapto-1-oxo-3-phenylpropyl)amino]-5-oxo-7H-pyrido[2,1-b][1,3]thiazepine-7-carboxylic acid which is currently undergoing clinical evaluation. This compound is reported herein as (1).

Robl discloses that the amino lactam portion of (1), i.e., the intermediate

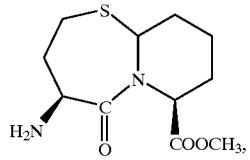

can be prepared by coupling (S)-2-amino-6,6-dimethoxyhexanoic acid methyl ester with the N-protected amino acid

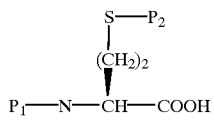

wherein $P_1$ is an amino protecting group and $P_2$ is a sulfur protecting group to give the dipeptide of the formula

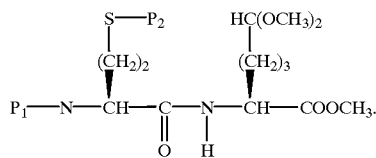

Removal of the $P_2$ protecting group, followed by acid catalyzed cyclization, and removal of the $P_1$ protecting group gives [4S-(4α,7α,10aβ)]-octahydro-4-amino-5-oxo-7H-pyrido[2,1-b][1,3]thiazephine-7-carboxdylic acid, methyl ester.

Robl discloses preparing (S)-2-amino-6,6-dialkoxyhexanoic acid, alkyl ester, such as (S)-2-amino-6,6-dimethoxyhexanoic acid, methyl ester, by converting N-protected L-ε-hydroxynorleucine to its methyl ester, oxidizing to a corresponding aldehyde, such as of the formula

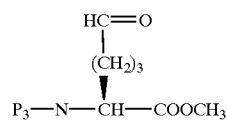

then reacting with trimethyl orthoformate in the presence of a strong acid catalyst, and removing the $P_3$ protecting group.

SUMMARY OF THE INVENTION

The present invention provides an enzymatic process for the preparation of the above-described intermediate, i.e., the protected amino lactam portion of (1).

More specifically, the present invention is directed to a process for preparing an amino lactam compound of the formula I

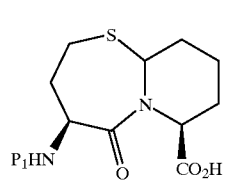

comprising contacting a dipeptide monomer of the formula II

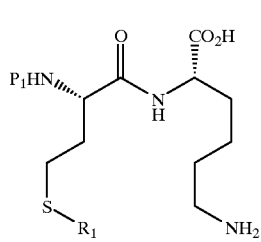

wherein $P_1$ is an amino protecting group, and $R^1$ is H, alkyl or of the formula

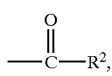

wherein R² is alkyl,
with an aminotransferase enzyme in the presence of α-ketoglutarate under conditions suitable for formation of the compound of formula I. The immediately preceding process will be referred to herein as the "oxidative deamination" process.

In an alternate embodiment, the oxidative deamination process is performed in the presence of a glutamate oxidase enzyme which functions to recycle glutamate formed during the process back to alpha-ketoglutarate.

The present invention is also directed to a process for preparing a dipeptide monomer starting compound of the formula III

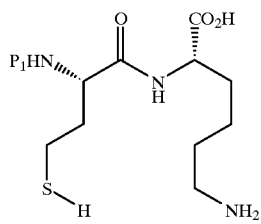

III comprising contacting a dipeptide dimer compound of the formula IV

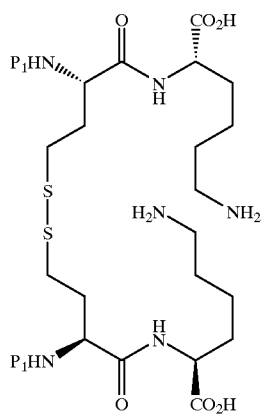

IV wherein $P_1$ is as defined above,
with a reducing agent under conditions suitable for formation of the compound of formula III. The immediately preceding process for preparing the dipeptide monomer will be referred to herein as the "reduction" process.

The present invention also concerns an engineered host cell containing recombinant nucleic acid capable of expressing an aminotransferase enzyme. In addition, the invention concerns a novel aminotransferase from Spingomonas sp. and nucleic acid encoding same.

The present invention also concerns the novel compounds of formulas II, III and IV.

BRIEF DESCRIPTION OF THE DRAWING

FIG. 1: DNA sequence (SEQ.ID.NO:1) encoding the preferred aminotransferase of the invention from *Sphingomonas paucimobillis* ATCC 202027 and the amino acid sequence (SEQ.ID.NO.:2) of the preferred aminotransferase of the invention.

DETAILED DESCRIPTION OF THE INVENTION

In the above formulas the amino protecting group, $P_1$, is a group such as benzyloxycarbonyl, phenoxyacetyl, phenyl acetyl, phenylmethoxycarbonyl, t-butyloxycarbonyl or the like; or a group which together with the N-atom forms a protecting group such as phthalimido. The most preferred $P_1$ group is phenylmethoxycarbonyl which is sometimes referred to herein as "Cbz."

After formation of the compound of formula I, said compound can be deprotected by techniques well known in the art to afford the above described intermediate, i.e., the amino lactam portion of (1). For example, when $P_1$ is phenylmethoxycarbonyl, treatment with iodotrimethylsilane or t-butoxycarbonyl treatment with a strong acid such as hydrochloric acid can be employed; when $P_1$ is phenoxyacetyl or phenylacetyl, the deprotection can be done enzymatically using Penicillin G acylase or Penicillin v acylase, and the like.

Although it is possible to perform the reduction process, isolate the compound of the formula III, and subsequently perform the oxidative deamination process, it is preferred to perform both steps in the same reactive medium wherein all components necessary to produce the compound of the formula I starting with compound of the formula IV are present. In such a situation, the reduction process and oxidative deamination process can be viewed as part of a single process.

The term "alkyl" or "alk" as used herein alone or as a part of another group, denotes such optionally substituted, but preferably unsubstituted, straight and branched chain saturated hydrocarbon groups, preferably having 1 to 10 carbons in the normal chain. Exemplary unsubsituted such groups include methyl, ethyl, propyl, isopropyl, n-butyl, iso-butyl, t-butyl, pentyl, hexyl, isohexyl, heptyl, 4,4-dimethyl, pentyl, octyl, 2,2,4-trimethylpentyl, nonyl, decyl and the like. The alkyl groups may be substituted by appropriate substituents providing compounds suitable for use in the present invention. Exemplary substituents of the alkyl group include one or more, preferably three or fewer, chloro groups, bromo groups, or iodo groups. The alkyl groups of $R^1$ and $R^2$ are preferably unsubstituted lower alkyl and most preferably methyl.

The term "lower alkyl" as used herein denotes alkyl groups having 1 to 3 carbon atoms.

The aminotransferase enzyme employed in the present invention may be any aminotransferase enzyme capable of catalyzing the conversion of Compound II into Compound I. Optionally, a glutamate oxidase enzyme may be employed which can be any glutamate oxidase enzyme capable of converting glutamate to alpha-keto glutarate. Enzymatic or microbial materials as the source of either of the enzymes (i.e., the aminotransferase and/or glutamate oxidase) may be employed in the free state or immobilized on a support such as by physical absorption or entrapment.

Suitable enzymes, regardless of origin or purity, are those enzymes referred to as aminotransferase enzyme and glutamate oxidase enzymes. The enzymes employed may, for example, be an enzyme isolated from a microorganism such as by homogenizing cell suspensions, followed by disintegration, centrifugation, DEAE-cellulose chromatography, ammonium sulfate fractionation, chromatography using gel filtration media such as Sephacryl (crosslinked co-polymer of allyl dextran and N,N'-methylene bisacrylamide) chromatography, and ion exchange chromatography such as Mono-Q (anion exchanger which binds negatively charged biomolecules through quaternary amine groups) chromatography.

Alternatively, the oxidative deamination process may use intact cells or cell extracts as a source of the enzyme(s). With respect to the use of microorganisms, the process of the present invention may be carried out using any suitable microbial materials capable of catalyzing the desired reaction. For example, the cells may be used in the form of intact wet cells or dried cells such as lyophilized, spray-dried or heat-dried cells, or in the form of treated cell material such as ruptured cells or cell extracts. Suitable microorganisms include genera from bacteria, yeasts and fungi that contain either endogenous or recombinant nucleic acid encoding either or both of the aminotransferase and glutamate oxidase enzymes. Examples of suitable organisms include: Bacillus sp. such as *B. subtilis*; Sporosarcina sp.; *Escherichia coli*, Pichia sp. such as *Pichia pastoris*; Thermoactmomyces sp. such as *T. intermedius*; Pseudomonas sp.; Spingomonas sp. such as *Spingomonas paucimobilis*; Streptomyces sp. such as *Streptomyces noursei*; Candida sp.; Saccharomyces sp.; Cephalosporium sp.; Fusarium sp.; Penicillium sp.; and the like.

The use of genetically engineered organisms is specifically contemplated. The host cell may be any cell, e.g., the ones mentioned in the immediately preceding paragraph such as *Escherichia coli, Pichia pastoris*, Streptomyces Sp., and the like, modified to contain a gene or genes for expressing one or more aminotransferases and/or glutamate oxidases capable of catalysis as described herein.

It is particularly preferred to employ microorganisms of the Pseudomonas and Sphingomonas genera, particularly the species *Sphingomonas paucimobilis*, especially the strain *Sphingomonas paucimobilis* ATCC 202027 (formerly known as Pseudomonas SC 16133) for the source of the aminotransferase. It is particularly preferred to employ microorganisms of the genus Streptomyces, as the source of the glutamate oxidase. The term "ATCC" as used herein refers to the accession number of the American Type Culture Collection, 10801 University Boulevard, Manassas, Va. 20110-2209. *Sphingomonas paucimobilis* ATCC 202027 was deposited with the ATCC on Sep. 9, 1997, under the provisions of the Budapest Treaty.

A commercial source of a glutamate oxidase useful in the oxidative deamination process is Sigma Chemical Co., St. Louis, Mo., product number GO400.

The oxidative deamination process of the present invention may be carried out subsequent to the fermentation of the microorganism(s) employed (two-stage fermentation and conversion), or concurrently therewith, that is, in the latter case, by in situ fermentation and reduction (single-stage fermentation and reduction). In the single-stage process, the microorganisms may be grown in an appropriate medium until sufficient growth of the microorganisms is attained. A compound of formula II may then be added to the microbial cultures and the oxidative deamination continued with the fermentation, preferably until complete conversion to the compound of formula I is obtained.

In the two-stage process, the microorganisms may, in the first stage, be grown in an appropriate medium for fermentation until exhibiting the desired enzymatic activity. Subsequently, the cells may be harvested by centrifugation and microbial cell suspensions prepared by suspending harvested cells in an appropriate buffered solution. Buffers such as Tris-HCl, phosphates, sodium acetate and the like may be used. Water may also be used to prepare suspensions of microbial cells. In the second stage, the compound of formula II may be mixed with the microbial cell suspensions, and the enzymatic conversion of the compound catalyzed by the microbial cell suspension. The reaction is preferably conducted until all or nearly all of the compound of formula II is converted to the compound of formula I.

Growth of the microorganisms may be achieved by one of ordinary skill in the art by the use of an appropriate medium. Appropriate media for growing microorganisms include those which provide nutrients necessary for the growth of the microbial cells. A typical medium for growth includes necessary carbon sources, nitrogen sources, and trace elements. Inducers may also be added. The term "inducer", as used herein, includes any compound enhancing formation of the desired enzymatic activity within the microbial cell, such as those compounds containing L-lysine and L-lysine analogs. Formula I compounds may be added as inducers during growth of the microorganism.

Carbon sources may include sugars such as maltose, lactose, glucose, fructose, glycerol, sorbitol, sucrose, starch, mannitol, propylene glycol, and the like; organic acids such as sodium acetate, sodium citrate, and the like; amino acids such as sodium glutamate, and the like; and alcohols such as methanol, ethanol, propanol, and the like.

Nitrogen sources may include N-Z amine A, corn steep liquor, soy bean meal, beef extracts, yeast extracts, yeastamin, molasses, baker's yeast, tryptone, nutrisoy, peptone, sodium nitrate, ammonium sulfate, and the like.

Trace elements may include phosphates and magnesium, manganese, calcium, cobalt, nickel, iron, sodium and potassium salts.

The medium employed may include more than one carbon or nitrogen source or other nutrient.

A preferred medium for Streptomyces sp. is an aqueous medium having the following components (in weight %):

| Component | |
|---|---|
| Nutrisoy | 3% |
| Maltrin M 180 | 1% |

A preferred medium for *Sphingomonas paucimobilis* ATCC 202027 is an aqueous medium having the following components (in weight %):

| Component | |
|---|---|
| Peptone | 1.5% |
| Yeast Extract | 1.0% |
| $KH_2PO_4$ | 0.2% |
| $K_2HPO_4$ | 0.2% |
| $MgSO_4$ | 0.01% |
| NaCl | 0.2% |

A preferred medium for *E. coli* is an aqueous medium having the following components (in weight %):

| Component | |
|---|---|
| NZ Amine A | 1% |
| Yeastamin | 2% |
| Glycerol | 2% |
| Na$_2$HPO$_4$ | 0.6% |
| K$_2$HPO$_4$ | 0.3% |
| (NH$_4$)$_2$SO$_4$ | 0.125 |
| Propylene glycol | 0.05% |
| MgSO$_4$ · 7H$_2$O | 0.0246% |
| Kanamycin | 0.005% |
| pH 7.0–7.2 | |

The pH of the medium is preferably adjusted to about 6 to 8, depending upon the particular medium, sterilized, e.g., at a temperature of 121° C. for 30 minutes, and then adjusted to a desirable pH after sterilization.

When growing microorganisms, the oxidative deamination process of the invention is preferably carried out under aerobic conditions. The agitation and aeration of the reaction mixture affects the amount of oxygen available during the process which may be conducted, for example, in shake-flask cultures or fermentor tanks during growth of microorganisms in a single-stage or two-stage process. The agitation range from 50 to 500 RPM is preferable, with 50 to 100 RPM being most preferred. Aeration of about 0.1 to 10 volumes of air per volume of media per minute (i.e., 0.1 to 10 v/vt) is preferred, with aeration of about 5 volumes of air per volume of media per minute (i.e., 5 v/vt) being most preferred.

If the oxidative deamination process is performed in a second stage after growth of the microorganisms, oxygen is not known to be required and may be detrimental.

The oxidative deamination process of the present invention is carried out using alpha-ketoglutarate and, optionally, a glutamate oxidase enzyme. The glutamate oxidase catalyzes the reaction of glutamate to form alpha-ketoglutarate and thereby providing a means of recycling the alpha-ketoglutarate. The alpha-ketoglutarate functions as an acceptor of the amino group of the compound of formula II.

In the oxidative deamination process the compound of the formula II is converted to the compound of the formula I via two intermediates which spontaneously convert to form Compound I, which is illustrated by the following reaction scheme:

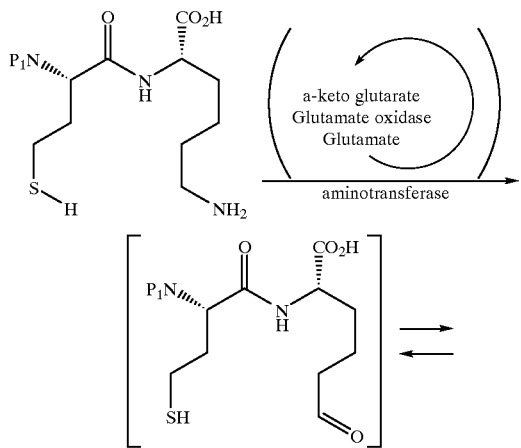

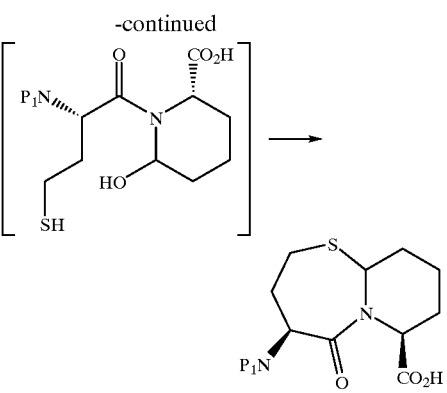

In the oxidative deamination process, the compound of the formula II with a free sulfhydryl, S-alkyl, or S-acetyl can be employed. In case of the S-alkylated compound of the formula II, the alkyl group is first removed either chemically or enzymatically and converted to a compound of the formula II with free sulfhydryl and is then used in the enzymatic process. In case of the S-acetyl compound of the formula II, the basic reaction conditions causes hydrolysis of the acetyl group to generate the desired compound of the formula II with a free sulfhydryl group.

It is preferred to employ an aqueous liquid as the reaction medium, although an organic liquid, or a miscible or immiscible (biphasic) organic/aqueous liquid mixture may also be employed.

It is preferred to employ 0.1 to 25 weight % of the compound of formula II starting material based on the combined weight of the compound and reaction medium. The amount of enzyme or microorganism employed relative to the starting material is selected to allow catalysis of the oxidative deamination process.

The products of the oxidative deamination process of the present invention may be isolated and purified, if desired, by known methodologies such as by extraction distillation, crystallization, column chromatography, and the like.

A preferred method for separating the desired compound of formula I from the remaining compounds of the reaction medium is concentration by removal of water, then addition of methanol to crystallize out the amino acid.

Preferred aminotransferases useful herein are selected from those amino transferases known as Epsilon aminotransferases and L-α-aminotransferases.

Specific examples include aspartate aminotransferases, glutamate aminotransferases, pyrurate aminotransferases, ornithine aminotransferases, branch-chain aminotransferases, and the like. The most preferred aminotransferase has the sequence shown in FIG. 1 (SEQ.ID.NO.:2). Other preferred aminotransferases have at least 80% identity to SEQ.ID.No.:2, more preferably at least 90% identity to SEQ.ID.NO.:2. Glutamate oxidase is commercially available from Streptomyces sp. (Sigma Chemicals, Product #G0400).

The present invention also contemplates use of two or more aminotransferases and/or two or more glutamate oxidases, particularly when using whole cells or crude extracts. The amino transferases and glutamate oxidases, useful in the present invention are typically from a variety of plant, animal, and microbial origins. Alternatively, the enzymes useful in the present invention may be obtained by synthetic means, i.e., chemical synthesis of the polypeptide from its component amino acids, by methods known to those of ordinary skill in the art. For example, the solid phase procedure described in Houghton et al., Proc. Natl. Acad. Sci. 82, 5131–5135 (1985) may be employed. The enzymes may be obtained by production in prokaryotic or eukaryotic host cells expressing a DNA sequence coding for the desired enzyme (endogenous or recombinant), or by in vitro translation of the mRNA encoded by a DNA sequence coding for all or part of the desired enzyme. Techniques for the production of polypeptides by these means are known in the art, and are described herein.

Conditions for the enzymatic oxidative deamination process can vary widely depending on the type and form of enzyme employed.

The oxidative deamination process of the present invention is performed under conditions suitable for forming the desired compound of formula I. The pH of the medium is preferably maintained between about 4 and 12, more preferably between about 6 and 8, during the growth of microorganisms. During the process, whether performed with enzymes or microorganisms, the pH is maintained between about 6 and 10, preferably between about 7 and 9.

Temperature is a measure of the heat energy available for the oxidative deamination process, and should be maintained to ensure that there is sufficient energy available for this process. A suitable temperature range for the process of the invention is from about 15° C. to about 60° C. A preferred temperature range is from about 25° to about 40° C. If the process involves active fermentation, a suitable temperature range is about 35° C. to about 45° C., preferably about 40° C. A typical reaction time is about 4 to about 48 hours, preferably about 4 to 8 hours, measured from the time of initially treating the compound of formula II with a microorganism(s) or enzyme(s) as described herein. It is preferred that complete or substantially complete conversion of the compound of formula II takes place.

Pressure is not known to be critical to practice of the invention and for convenience about atmospheric pressure is typically employed. A broad pH range for the process is about 6 to about 10, preferably about 7 to about 9, regardless of whether active fermentation is employed.

The oxidation deamination process of the present invention results in high yield of the compound of Formula I and Formula III. A typical yield is greater than about 70%, preferably greater than about 80%, more preferably greater than about 90%, and most preferably about 95%.

It is preferable to actively terminate the oxidative deamination process. The reaction can be terminated by adding an effective amount of acid to the reaction mixture. Preferred acids are strong acids such as trichloroacetic acid (TCA), methane sulfonic acid, phosphoric acid, acetic acid, hydrochloric acid, sulfuric acid, and the like. An effective amount of acid is sufficient to lower pH to about 2; e.g., about 5% to 20% acid, preferably about 10% acid.

To prepare the starting dipeptide dimer of formula IV in the reduction process, L-homocystine is reacted with an appropriate protecting group halide (e.g., CBZ-Cl) to form a protected L-homocystine of the formula

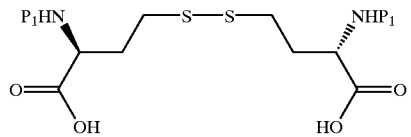

For CBZ protected L-homocystine, the following scheme is illustrated:

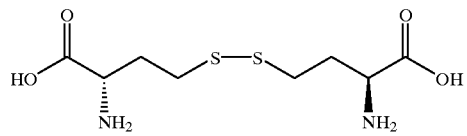

L-Homocystine
MW 268.35
99.9 HI

1) NaOH
   H$_2$O
   CBZ-Cl
2) MTBE
3) HCl
4) H$_2$O
   heptanes

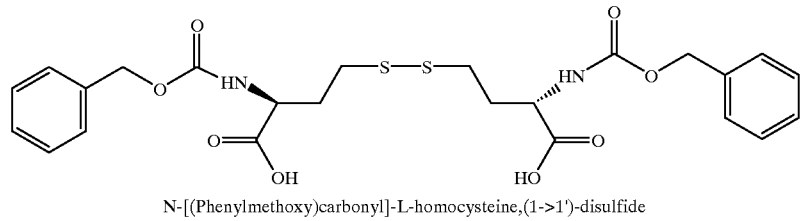

N-[(Phenylmethoxy)carbonyl]-L-homocysteine,(1->1')-disulfide

The protected L-homocystine is then reacted with and dicyclohexyl carbodimide (DCC) to form N-[(Phenylmethoxy)carbonyl]-L-homocysteine, (1→1')-disulfide. The compound so formed is then reacted with N-MBOC-L-Lysine to form the dipeptide dimer of Formula IV. The compound of Formula IV is then contacted with a reducing agent under conditions suitable for formation of the compound of formiua III. Reducing agents include dithiothreitol (DTT), 2-mercaptoethanol, tributylphosphine, and the like. For CBZ protected compounds, the following scheme is illustrated:

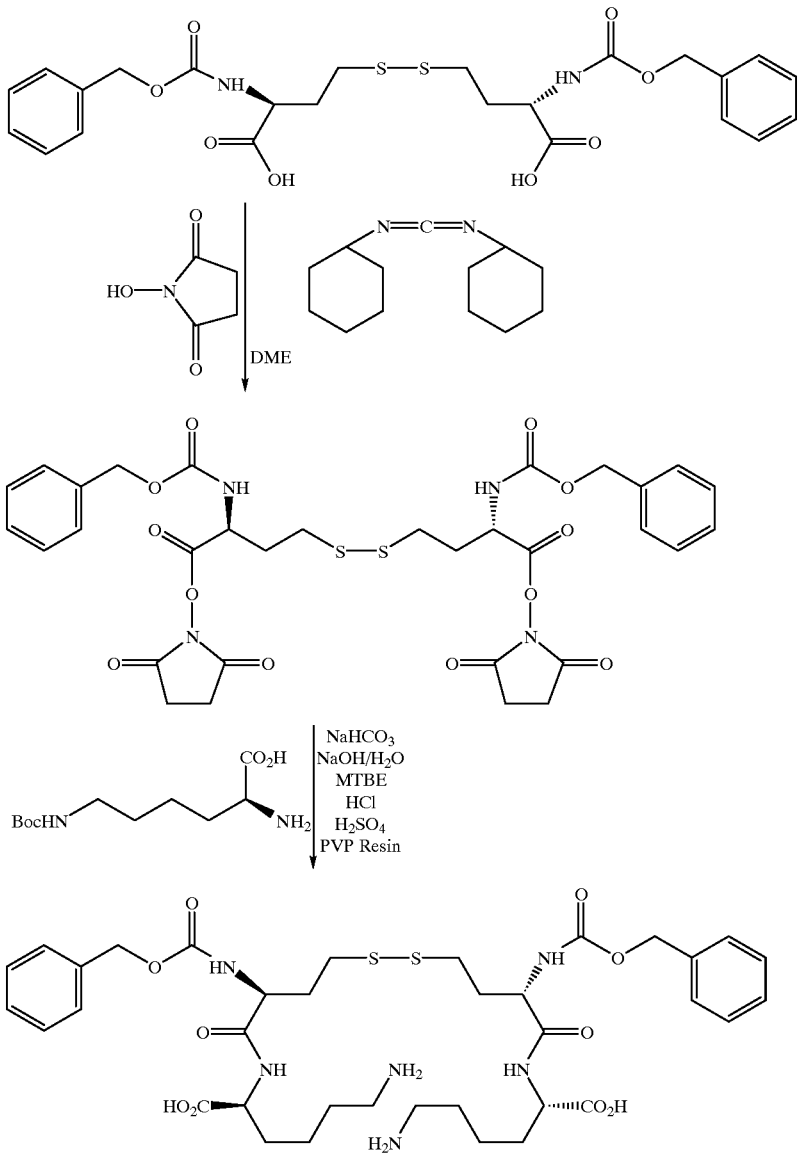

Suitable conditions for the reduction process include a temperature of about 25° C. to about 40° C., a reaction time of about 5 minutes to about 1 hour, and a pH of about 7 to about 9. Suitable solvents for the reduction process include water;water containing 10% solvent, such as ethanol, methanol, or acetonitrile; and the like.

As described by Robl in U.S. Pat. No. 5,508,272, (S)-2-amino-6,6-dimethoxyhexanoic acid, methyl ester of formula X can be coupled with the N-protected amino acid of the formula V

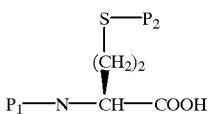

to give the dipeptide of the Formula VI

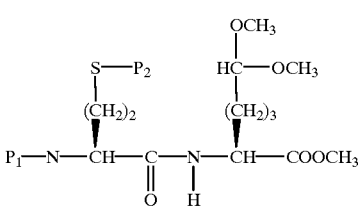

wherein $P_1$ is an amino protecting group such as benzyloxycarbonyl or t-butyloxycarbonyl, phenoxyacetyl, phenylacetyl, or a group which together with the N-atom forms a protecting group such as phthalimido and $P_2$ is a mercapto protecting group such as acetyl or benzoyl. This coupling reaction is preferably performed in the presence of a coupling reagent such as benzotriazol-1-yloxytris(dimethylamino)phosphonium hexafluorophosphate, ethyl- 3-(3-dimethyl-amino)propyl carbodiimide, dicyclohexylcarbodiimide, or methanesulfonyloxybenzotriazole.

The $P_2$ protecting group is selectively removed from the dipeptide of formula VI such as by treatment with sodium methoxide in methanol or by treatment with p-toluenesulfonic acid in methanol. The resulting mercaptan compound is then subjected to an acid catalyzed cyclization reaction preferably by treating with a strong acid such as trifluoroacetic acid, p-toluenesulfonic acid, methanesulfonic acid, or a commercially available polystyrene sulfonate polymer type ion exchange resin such as Amberlyst15®. This cyclization reaction can be performed in a non-protic solvent such as methylene chloride or chloroform to give the lactam of the formula VII

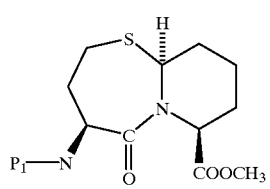

VII

The lactam of formula VII is then treated to remove the $P_1$ N-protecting group and then reacted with the acylmercaptoalkanoyl sidechain of the formula VIII

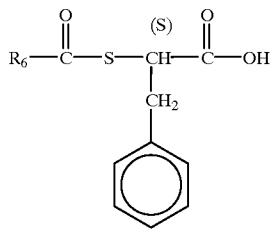

VIII wherein $R_6$ is methyl or phenyl giving the compound of the formula IX

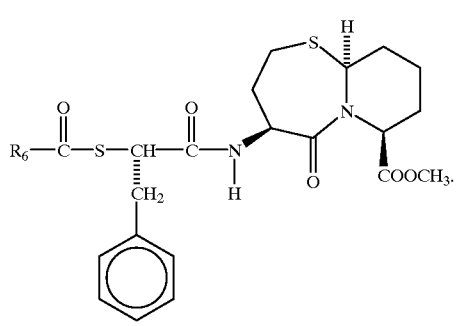

IX

This coupling reaction can be per formed in an organic solvent such as methylene chloride and in the presence of a coupling reagent such as 1-ethyl-3-(3-dimethylamino-propyl)carbodiimide, dicyclohexylcarbodiimide, benzotriazol-1-yloxytris-(dimethylamino)phosphonium hexafluorophosphate, or carbonyldiimidazole. Alternatively, the acylmercaptoalkanoic acid of formula VIII can be converted to an activated form prior to coupling such as an acid chloride, mixed anhydride, symmetrical anhydride, activated ester, etc.

The $P_1$ N-protecting group can be removed from the lactam of formula VII, for example, by treatment with hydrazine monohydrate when $P_1$ together with the N-atom forms a phthalimido group or by treatment with iodotrimethylsilane or palladium on carbon and hydrogen when $P_1$ is benzyloxycarbonyl or by treatment with hydrochloric acid in dioxane or other strong acid when $P_1$ is t-butoxycarbonyl.

The acyl group $R_6$—C(O)— is removed and the methyl ester group is converted to the carboxylic acid from the compound of formula IX to give the desired final product of formula XI. For example, when $R_6$ is methyl treatment with methanolic sodium hydroxide followed by aqueous acid yield the desired compound of formula XI.

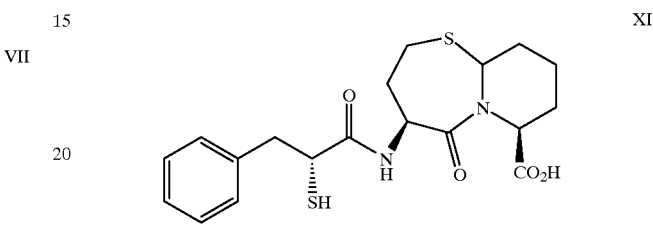

XI

4S-[4α(R*),7α,10aβ]]-Octahydro-4-[(2-mercapto-1-oxo-3-phenylpropyl)amino]-5-oxo-7H-pyrido[2,1-b][1,3]thiazepine-7-carboxylic acid possesses angiotensin converting enzyme and neutral endopeptidase inhibitory activity. This compound as well as its pharmaceutically acceptable salts are useful in treating cardiovascular diseases such as hypertension and congestive heart failure as noted in Robl U.S. Pat. No. 5,508,272. This compound can be administered to a mammalian host such as man at from about 0.1 mg to about 100 mg per kg of body weight per day, preferably from about 0.5 mg to about 25 mg per kg of body weight per day. The compound is preferably administered orally but parenteral routes and topical routes can also be employed. The daily dose can be administered singly or can be divided into two to four doses administered throughout the day.

The present invention also concerns an engineered host cell comprising a recombinant nucleic acid sequence coding for aminotransferase derived from *Sphingomonas paucimobilis* ATCC 202027 (preferably SEQ.ID.NO.:1). Preferably, the nucleic acid molecules are DNA molecules and the nucleic acid sequences are DNA sequences.

As used in the present application, the term "modified", when referring to a nucleotide or polypeptide sequence, means a nucleotide or polypeptide sequence which differs from the wild-type sequence found in nature.

The recombinant host cell of the present invention can be any microorganism that is capable of producing recombinant aminotransferase and is capable of being transformed or genetically engineered with aminotransferase from a different species to express catalytically active aminotransferase. Examples of host cells of the invention include, for example, Bacillus such as *B. subtilis; Sporosarcina; Escherichia coli*; Pichia such as *Pichia pastoris*; Thermoactmomyces such as *T. intermedius*, Pseudomonas.; Sphingomonas such as *Sphingomonas paucimobilis*; Streptomyces such as *Streptomyces noursei*; Candida; Saccharomyces, Cephalosporium.; Fusarium ; Penicillium ; and the like. A preferred host cell of the invention is *Escherichia coli*.

All DNA sequences are represented herein by formulas whose left to right orientation is in the conventional direction of 5' to 3'. Nucleotide base abbreviations used herein are conventional in the art, i.e., T is thymine, A is adenine, C is cytosine, and G is guanine; also, X is A,T,C, or G, Pu is purine (i.e., G or A), and Py is pyrimidine (i.e., T or G). Further preferred as the DNA for the recombinant aminotransferase is a DNA sequence having all or part of the nucleotide sequence substantially as shown in FIG. 1; or a DNA sequence complementary to this DNA sequence; or a DNA sequence which hybridizes to a DNA sequence complementary to one of these DNA sequences. Preferably, the DNA sequence hybridizes under stringent conditions. Stringent hybridization conditions select for DNA sequences of greater than 80% identity, preferably greater than 85% or, more preferably, greater than 90% identity. Screening DNA under stringent conditions may be carried out according to the method described in Nature, 313: 402–404 (1985). The DNA sequences capable of hybridizing under stringent conditions with the DNA disclosed in the present application may be, for example, allelic variants of the disclosed DNA sequences, or may be derived from other bacterial, fungal or yeast sources. General techniques of nucleic acid hybridization are disclosed by Sambrook et.al., In: Molecular Cloning, a Laboratory Manual, 2d edition, Cold Spring Harbor Laboratory, Cold Spring Harbor, N.Y. (1984), and by Haymes et al., In: Nucleic Acid Hybridization, a Practical Approach, IRL Press, Washington, D.C. (1985), which references are incorporated herein by reference. Stringent hybridization conditions are described in Hames et al. at pages 119–121 as the following: Incubation in 4×SET buffer, 10×Denhardt's solution, 0.1% SDS, 0.1% sodium pyrophosphate, 50 µg/ml denatured salmon sperm DNA at 68° C. for 16–24 hours; followed by washing three times for 20 minutes in 3×SET, 0.1% SDS, 0.1% sodium pyrophosphate at 68° C., washing twice for 20 minutes in 1×SET, 0.1% SDS, 0.1% sodium pyrophosphate at 68° C., washing once for 20 minutes in 0.1×SET, 0.1% SDS, 0.1% sodium pyrophosphate at 68° C., and washing once for 20 minutes in 4×SET at room temperature. In the case of a nucleotide sequence (e.g., a DNA sequence) coding for part of the enzyme, it is required that the nucleotide sequence code for a fragment that is catalytically active, i.e. has enzymatic activity.

The preferred DNA encoding aminotransferase has the sequence of SEQ.I.D. No. 1, its complement, or a DNA molecule capable of hybridyzing under stringent conditions to a DNA having the sequence of SEQ. I.D. NO:1 or its complement. The preferred aminotransferase of the invention has the amino acid sequence of SEQ. I.D. NO:2 or an amino acid sequence having at least 80% identity to SEQ.I.D. NO:2, more preferably at least 90% identity.

The variant amino acid or DNA sequences within the scope of the invention are homologous to the sequences specifically disclosed herein. The degree of homology (percent identity) between a specifically disclosed and a variant sequence may be determined, for example, by comparing the two sequences using the GAP computer programs, version 6.0, described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl Math* 2:482,1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

The aminotransferase sequence(s) of the present invention used to transform the host cell(s) can be obtained using various methods well-known to those of ordinary skill in the art. At least three alternative principal methods may be employed:

(i) the isolation of a double-stranded DNA sequence from genomic DNA or complementary DNA (cDNA) which contains the sequence;

(2) the chemical synthesis of the DNA sequence; and (3) the synthesis of the DNA sequence by polymerase chain reaction (PCR).

In the first approach, a genomic or cDNA library can be screened in order to identify a DNA sequence coding for all or part of aminotransferase. For example, a *Sphingomonas paucimobilis* genomic DNA library can be screened in order to identify the DNA sequence coding for all or part of aminotransferase. Various techniques can be used to screen the genomic DNA or cDNA libraries.

For example, labeled single stranded DNA probe sequences duplicating a sequence present in the target genomic DNA or cDNA coding for all or part of aminotransferase can be employed in DNA/DNA hybridization procedures carried out on cloned copies of the genomic DNA or cDNA which have been denatured to single stranded form.

A genomic DNA or cDNA library can also be screened for a genomic DNA or cDNA coding for all or part of aminotransferase using immunoblotting techniques.

In one typical screening method suitable for either immunoblotting or hybridization techniques, the genomic DNA library, which is usually contained in a vector, or cDNA library is first spread out on agar plates, and then the clones are transferred to filter membranes, for example, nitrocellulose membranes. A DNA probe can then be hybridized or an antibody can then be bound to the clones to identify those clones containing the genomic DNA or cDNA coding for all or part of aminotransferase.

In the second approach, the DNA sequences of the present invention coding for aminotransferase can be chemically synthesized. For example, the DNA sequence coding for aminotransferase can be synthesized as a series of 100 base oligonucleotides that can be sequentially ligated (via appropriate terminal restriction sites or complementary terminal sequences) so as to form the correct linear sequence of nucleotides.

In the third approach, the DNA sequences of the present invention coding for aminotransferase can be synthesized using PCR. Briefly, pairs of synthetic DNA oligonucleotides at least 15 bases in length (PCR primers) that hybridize to opposite strands of the target DNA sequence are used to enzymatically amplify the intervening region of DNA on the target sequence. Repeated cycles of heat denaturation of the template, annealing of the primers and extension of the 3'-termini of the annealed primers with a DNA polymerase results in amplification of the segment defined by the 5' ends of the PCR primers. See, White et al., Trends Genet. 5, 185–189 (1989).

The DNA sequences useful in the present invention coding for aminotransferase can also be modified (i.e., mutated) to prepare various mutations. Such mutations may be either degenerate, i.e., the mutation changes the amino acid sequence encoded by the mutated codon, or non-degenerate, i.e., the mutation does not change the amino acid sequence encoded by the mutated codon. These modified DNA sequences may be prepared, for example, by mutating the aminotransferase DNA sequence so that the mutation results in the deletion, substitution, insertion, inversion or addition of one or more amino acids in the encoded polypeptide using various methods known in the art. For example, the methods of site-directed mutagenesis described in Morinaga et al., Bio/Technol. 2, 636–639 (1984), Taylor et al., Nucl. Acids Res. 13, 8749–8764 (1985) and Kunkel, Proc. Natl. Acad. Sci. USA 82, 482–492 (1985) may be employed. In addition, kits for site-directed mutagenesis may be purchased from commercial vendors. For example, a kit for performing site-directed mutagenesis may be purchased from Amersham Corp. (Arlington Heights, Ill.). In addition, disruption, deletion and truncation methods as described in Sayers et al., Nucl. Acids Res. 16, 791–802 (1988) may also be employed. Both degenerate and non-degenerate mutations may be advantageous in producing or using the polypeptides of the present invention. For example, these mutations may permit higher levels of production, easier purification, or provide additional restriction endonuclease recognition sites. All such modified DNA and polypeptide molecules are included within the scope of the invention.

The host cells of the invention can be conveniently transformed by use of expression vectors comprising a DNA sequence coding for aminotransferase. The expression vectors preferably contain all or part of one of the DNA sequences having the enzyme(s) nucleotide sequence substantially as shown in Takada, H., et al, *J. Biochem.*, 109, 371–376 (1991). Further preferred are expression vectors comprising one or more regulatory DNA sequences operatively linked to the DNA sequence coding for all or part of aminotransferase. As used in this context, the term "operatively linked" means that the regulatory DNA sequences are capable of directing the replication and/or the expression of the DNA sequence coding for aminotransferase.

Expression vectors of utility in the present invention are often in the form of "plasmids", which refer to circular double stranded DNA loops which, in their vector form, are not bound to the chromosome. However, the invention is intended to include such other forms of expression vectors which serve equivalent functions and which become known in the art subsequently hereto.

Expression vectors useful in the present invention typically contain an origin of replication, a promoter located in front (i.e., upstream of) the DNA sequence (preferably an inducible promoter such as tac or bacteriophage λpL) and followed by the DNA sequence coding for all or part of aminotransferase. The DNA sequence coding for all or part of aminotransferase is followed by transcription termination sequences and the remaining vector. The expression vectors may also include other DNA sequences known in the art, for example, stability leader sequences which provide for stability of the expression product, secretory leader sequences which provide for secretion of the expression product, sequences which allow expression of the structural gene to be modulated (e.g., by the presence or absence of nutrients or other inducers in the growth medium), marker sequences which are capable of providing phenotypic selection in transformed host cells, stability elements such as centromeres which provide mitotic stability to the plasmid, and sequences which provide sites for cleavage by restriction endonucleases. The characteristics of the actual expression vector used must be compatible with the host cell which is to be employed. For example, when cloning in a fungal cell system, the expression vector should contains promoters isolated from the genome of fungal cells (e.g., the trpC promoter from *Aspergillus nidulans*, the AOX1 promoter from *Pichia pastoris*, and the GAP promoter from *P. pastoris*). Certain expression vectors may contain an autonomously replicating sequence (ARS; e.g., ARS from *Fusarium oxysporum, Saccharomyces cerevisiae*, and the like) which promotes in vivo production of self-replicating plasmids in fungal hosts. It is preferred that the yeast expression vectors of the invention do not have a yeast ARS sequence and thus will integrate into host chromosomes upon plasmid entry of host cells. Such integration is preferred because of enhanced genetic stability. An expression vector as contemplated by the present invention is at least capable of directing the replication in and integration in fungal cells, and preferably the expression, of the PDH DNA sequence disclosed in Takada, H., et al, J. Biochem., 109, 371–376 (1991) in Pichia cells. Suitable promoters include, for example, the trpC promoter from *Aspergillus nidulans*, the penicillin V amidase promoter from *F. oxysporum*, and the AOX promoter from *P. pastoris*. Suitable termination sequences include, for example, the trpC terminator from *A. nidulans*, the PVA terminator for *F. oxysporum*, and the AOX1 transcription termination sequence of *P. pastoris*. It is also preferred that the expression vector include a sequence coding for a selectable marker. The selectable marker is preferably antibiotic resistance. As selectable markers, G418 resistance can be conveniently employed. All of these materials are known in the art and are commercially available.

Preferably, the host cell in which the DNA sequence encoding the enzyme is cloned and expressed is a prokaryotic such as *E. coli*. For example, *E. coli* K12 strain 294 (ATCC 31446), *E. coli* B, *E. coli* X1776 (ATCC 31537), *E. coli* strain ST9 or *E. coli* JM 101 can be employed. Other prokaryotes can also be used; for example, bacilli such as *Bacillus subtilis* and enterobacteriaceae such as *Salmonella typhimurium* or *Serratia marcesans*.

In general, where the host cell is a prokaryote, expression or cloning vectors containing replication and control sequences which are derived from species compatible with the host cell are used. The vector may also carry marking sequences which are capable of providing phenotypic selection in transformed cells. For example, *E. coli* has commonly been transformed using pBR322, a plasmid derived from an *E. coli* species (Bolivar et al., Gene 2:95 (1977)). pBR322 contains genes for ampicillin and tetracycline resistance and thus provides easy means for identifying transformed cells.

For use in expression, the plasmid including the DNA to be expressed contains a promoter. Those promoters most commonly used in recombinant DNA construction for use with prokaryotic hosts include the lactamase (penicillinase) and lactose promoter systems (Chang et al, *Nature,* 275:615 (1978); Itakura et al. *Science,* 198:1056 (1977); Goeddel et al., *Nature* 281:544 (1979)) and a tryptophan (trp) promoter system (Goeddel et al. *Nucleic Acids Res.,* 8:4057 (1980); EPO Publ. No. 0036776). While these are the most commonly used, other microbial promoters such as the tac promoter (Amann et al., *Gene* 25,167–178 (1983)) have been constructed and utilized, and details concerning their nucleotide sequences have been published, enabling a skilled worker to ligate them functionally in operable relationship to genes in vectors (Siebenlist et al. *Cell* 20:269 (1980)).

Particularly preferred are the expression vectors designated pAL 781-LAT described herein below, which contain the DNA sequence coding for aminotransferase, or expression vectors with the identifying characteristics of these plasmids.

Suitable expression vectors containing the desired coding and control sequences may be constructed using standard recombinant DNA techniques known in the art, many of which are described in Sambrook et al. Molecular Cloning: A Laboratory Manual, 2nd edition, Cold Spring Harbor Laboratory, Cold Spring Harbor, N.Y. (1989).

The host cells of the invention preferably contain an expression vector comprising one or more regulatory DNA sequences capable of directing the replication and/or the expression of and operatively linked to a DNA sequence coding for all or part of aminotransferase.

Expression vectors may be introduced into host cells by various methods known in the art. For example, transformation of host cells with expression vectors can be carried out by the polyethylene glycol mediated protoplast transformation method. However, other methods for introducing expression vectors into host cells, for example, electroporation, biolistic injection, or protoplast fusion, can also be employed.

Once an expression vector has been introduced into an appropriate host cell, the host cell may be cultured under conditions permitting expression of large amounts of the desired polypeptide, in the preferred case a polypeptide molecule comprising aminotransferase.

Host cells containing an expression vector which contains a DNA sequence coding for all or part of aminotransferase may be identified by one or more of the following five general approaches: (a) DNA-DNA hybridization; (b) the presence or absence of marker gene functions; (c) assessing the level of transcription as measured by the production of mRNA transcripts in the host cell; (d) detection of the gene product immunologically; and (e) enzyme assay, enzyme assay being the preferred method of identification.

In the first approach, the presence of a DNA sequence coding for all or part of the desired enzyme can be detected by DNA-DNA or RNA-DNA hybridization using probes complementary to the DNA sequence.

In the second approach, the recombinant expression vector host system can be identified and selected based upon the presence or absence of certain marker gene functions (e.g., acetamide utilization, resistance to antibiotics, resistance to fungicide, uracil prototrophy, etc.). A marker gene can be placed in the same plasmid as the DNA sequence coding for all or part of the enzyme under the regulation of the same or a different promoter used to regulate the enzyme coding sequence. Expression of the marker gene in response to induction or selection indicates the presence of the entire recombinant expression vector which carries the DNA sequence coding for all or part of the desired enzyme.

In the third approach, the production of enzyme mRNA transcripts can be assessed by hybridization assays. For example, polyadenylated RNA can be isolated and analyzed by Northern blotting or nuclease protection assay using a probe complementary to the RNA sequence. Alternatively, the total nucleic acids of the host cell may be extracted and assayed for hybridization to such probes.

In the fourth approach, the expression of all or part of the desired enzyme can be assessed immunologically, for example, by Western blotting.

In the fifth approach, expression of the enzyme can be measured by assaying for enzyme activity using known methods.

The DNA sequences of expression vectors, plasmids or DNA molecules of the present invention may be determined by various methods known in the art. For example, the dideoxy chain termination method as described in Sanger et al., Proc. Natl. Acad. Sci. USA 74, 5463–5467 (1977), or the Maxam-Gilbert method as described in Proc. Natl. Acad. Sci. USA 74, 560–564 (1977).

It should, of course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

The present invention further concerns a method for producing aminotransferase comprising culturing an engineered host cell containing recombinant nucleic acid capable of expressing aminotransferase and containing an expression vector capable of expressing aminotransferase. Preferably the expression vector is pAL781-LAT.

All amino acid residues identified herein are in the natural L-configuration. In keeping with standard polypeptide nomenclature, J. Biol. Chem. 243, 3557–3559 (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

All amino acid sequences are represented herein by formulas whose left to right orientation is in the conventional direction of amino-terminus to carboxy-terminus.

It will be understood that allelic variations of the nucleic acid and amino acid sequences useful herein naturally exist, or may be intentionally introduced using methods known in the art. These variations may be demonstrated by one or more amino acid differences in the overall sequence, or by deletions, substitutions, insertions, inversions or additions of one or more amino acids in said sequence. Such amino acid substitutions may be made, for example, on the basis of similarity in polarity, charge, solubility, hydrophobicity, hydrophilicity and/or the amphiphatic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine, asparagine, glutamine, serine, threonine, phenylalanine, tyrosine. Other contemplated variations include salts and esters of the aforementioned polypeptides, as well as precursors of the aforementioned polypeptides, for example, precursors having N-terminal substituents such as methionine, N-formylmethionine and leader sequences. All such variations are included within the scope of the present invention.

The following examples illustrate the invention but should not be interpreted as a limitation thereon.

All references cited herein are incorporated by reference in their entirety.

EXAMPLE 1

Preparation of N-[(Phenylmethoxy)carbonyl]-L-homocysteine,(1->1')disulfide

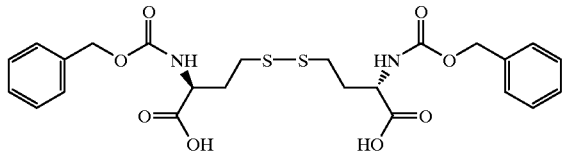

To a 3-L, 5-necked flask fitted with a mechanical stirrer, thermocouple, pH electrode, pressure equalized addition funnel with CBZ-Cl, and a second pressure equalized addition funnel with 1 N NaOH was charged 100.0 g (0.373 mol) L-homocystine and 1 L of 1 N NaOH (solution pH was 13.65). After cooling to 10° C., 117.0 mL (0.820 mol) CBZ-Cl was added dropwise over 15 minutes, maintaining the temperature at 10 to 16° C. When the pH of the mixture dropped to 11, 500 mL of NaOH were added dropwise. The pH after the addition of the 1 N NaOH was 7.89, requiring 16 mL of 10 N NaOH to raise the pH of the mixture to 11.90. After the reaction was judged complete by in-process HPLC analysis (<1% change in area counts of BMS-210474 disodium salt), 200 mL of MTBE were added and the mixture was agitated for about 15 minutes. After the phases were separated, the aqueous phase was extracted with two, 200-mL portions of MTBE. The aqueous solution was adjusted to pH 7.0 with 5.4 mL of concentrated HCl and the solution was sparged with nitrogen for 14 hours. The pH of the solution was further adjusted to 6.11 with 60 mL of 1 N HCl giving a very turbid suspension. The suspension was aged for 30 minutes, during which time the pH rose to 6.28. To the suspension was added 65 mL of N HCl, giving a pH of 6.18. 50 mL of concentrated HCl were added to give a pH of 5.5. 200 mL of methanol were added and the slurry was heated to 43° C. to break up any crystal aggregates. The pH was adjusted to 1.97 with 11 mL of concentrated HCl and the slurry was cooled to 20 to 25° C. After aging of the slurry for 2.5 hours, the crystals were collected by vacuum filtration. The filter cake was washed with three, 500-mL portions of water, followed by two, 250-mL portions of heptanes to dewater the cake. The product was dried under reduced pressure at NMT 55° C., returning 191.0 g (0.356 mol, 95.4 M %) as a white crystalline solid with a laboratory HPLC HI of 91.9

EXAMPLE 2

Preparation of $N^2$-[N-[(Phenylmethoxy)carbonyl]-L-homocysteinyl]-L-lysine,(1->1')-disulfide Procedure 1

To a 1-L, 3-necked flask equipped with a mechanical stirrer, thermocouple, and a nitrogen inlet and outlet is charged 30.00 g of N-[(Phenylmethoxy)carbonyl]-L-homocysteine, (1->1')-disulfide (55.91 mmol, 1 eg.), 14.10 g N-hydroxysuccinimide (123.00 mmol, 2.2 eq.) and 300 mL of DME. After the solution is cooled to -20 to -25° C., 29.99 g of DCC (145.37 mmol, 2.6 eq.) is added in one portion. The slurry is held at -25 to -10° C. until the reaction is judged complete by in-process HPLC assay (21 hours, 0 relative area percent N-[(Phenylmethoxy)carbonyl]-L-homocysteine, (1->1')-disulfide). The solids are filtered from the reaction and the filter cake is washed with two, 100-mL portions of DME. The solution is split into two, 250-mL portions.

To a 1-L, 5-necked flask equipped with a mechanical stirrer, thermocouple, pressure equalized addition funnel, and a nitrogen inlet and outlet is charged 9.40 g sodium bicarbonate (111.89 mmol, 4 eq.) and 200 mL of water. After dissolution of the bicarbonate, 17.21 g of N-MBoc-L-lysine (69.89 mmol, 2.5 eq.) is added. The slurry is adjusted to pH 11.11 with -10 mL of 10 N NaOH to dissolve the lysine. The solution is cooled to 0° C. and the 250 mL solution of the active ester is added dropwise over 2.25 hours while maintaining the reaction temperature at 0 to 5° C. After the reaction is judged complete by in-process HPLC analysis (~0.5 hours), the solids are filtered from the solution, and the cake is washed with two, 50-mL portions of DME. The reaction solution is extracted with two, 100-mL portions of MTBE. The product rich aqueous solution is diluted with 200 mL of MTBE and acidified to pH 1.64 with ~16 mL of concentrated HCl. The phases are split and the organic phase is washed with 100 mL of water. The organic phase is concentrated on a rotary evaporator to a white, crystalline solid of 28.08 g.

The solid is dissolved in 125 mL of DME and cooled to 0 to 5° C. 9 mL of concentrated sulfuric acid is added, maintaining the temperature below 15° C. After the addition is complete, the solution is warmed to 20 to 25° C. until the deprotection is judged complete by in-process HPLC analysis. After the reaction is complete (~0.75 hours), the solution is diluted with 150 mL of water and concentrated to ~one-half volume. The solution is diluted with 100 mL of water and extracted with two, 100 mL portions of MTBE.

The aqueous solution is added to ~400 g of PVP resin (2.5 eq. resin per eq. sulfuric acid) and the resin slurry is diluted with 200 mL of water and stirred with moderate agitation for 16 hours. The resin is removed by filtration over Hyflo and $N^2$-[N-[(Phenylmethoxy)carbonyl]-L-homocysteinyl]-L-lysine, (1->1')-disulfide is eluted with 500 mL portions of water. The fractions with HPLC HI>90 are combined (fractions 8 through 23), concentrated on a rotary evaporator, and lyophilized, to return 6.75 g (30.5 M %) of $N^2$-[N-[(Phenylmethoxy)carbonyl]-L-homocysteinyl]-L-lysine, (1->1')-disulfide with a laboratory HPLC HI of 96.4

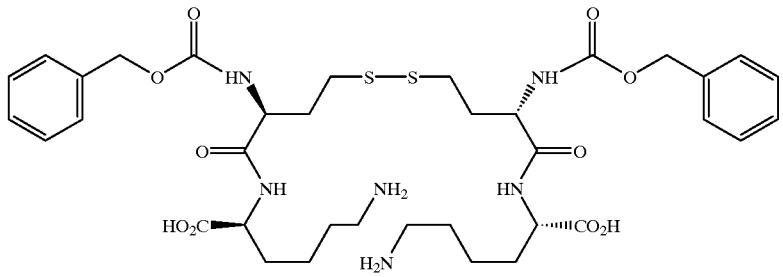

Procedure 2

Dicyclohexylcarbodimide (Aldrich, Lot KF 00929TZ; 4.82 g, 23.3 mmol) was added dropwise to a magnetically-stirred solution of L-CBZ-homocystine (6.22 g, 11.64 mmol) and N-hydroxysuccinimide (Aldrich, Lot JG 23818JG; 2.7 g, 23.3 mmol) in 1,2-dimethoxy ethane (50 mL) while the mixture is maintained at 0–5° C. The reaction mixture was stirred for 2 h at 0–5° C. and stored at 0° C. overnight. The reaction was followed by HPLC and determined to be complete after 18 h. The thick slurry was filtered and rinsed with 1,2-dimethoxy ethane (2×10 mL). The filtrate and the washings were combined and used "as is" in the next step.

A mechanically-stirred suspension of N-M-Boc-lysine (Sigma, Lot 73H0151; 5.74 g, 23.3 mmol) in water (55 mL) was cooled to 18° C. in an ice/water bath and 1N NaOH (24 mL, 24 mmol) was added to it. The bis active ester (37102-170-17) was added as a solution in DME (100 mL, 11.64 mmol) dropwise over 30 minutes between 20–23° C. The pH was maintained between 9 and 10 during the reaction by adding 1N NaOH. The reaction was followed by HPLC and determined to be complete after 1.5 h. The reaction mixture was then extracted with MTBE (2×20 mL) and the neutral MTBE extract was set aside. The aqueous layer was diluted with MTBE (50 mL) and acidified with 1N HCl between 0–5° C. to pH 2. The organic layer was separated and the aqueous layer was extracted with MTBE (2×30 mL). The MTBE extracts were combined, washed with water (2×40 mL) and concentrated. The weight of the residue, obtained as a crystalline foam, was 11.14 g. The protected peptide dimer was used as is in the next step.

Concentrated sulfuric acid (1.9 mL) was added to a magnetically-stirred solution of the protected peptide dimer (37102-171.22; 6 g, 6.04 mmol) in DME (20 mL) with cooling at 22° C. The reaction was followed by HPLC and found complete after 2 h. The reaction mixture was poured into 2:1.5 water:DME (35 mL) and extracted with MTBE (2×15 mL). The aqueous phase was adjusted to pH 4.25 using 10N NaOH. The HPLC of the aqueous phase showed 2 main peaks corresponding to $N^2$-[N-[(Phenylmethoxy) carbonyl]-L-homocysteinyl]-L-lysine, (1->1')-disulfide (76 HI) and the monolysine adduct (19 II). The aqueous solution of $N^2$-[N-[(Phenylmethoxy)carbonyl]-L-homocysteinyl]-L-lysine, (1->1')-disulfide was then passed through a column of PVP resin (60 g) to remove sulfuric acid. The column was eluted with water and fractions 2 to 10 (75 mL each) were pooled and concentrated. The concentrated aqueous solution of $N^2$-[N-[(Phenylmethoxy)carbonyl]-L-homocysteinyl]-L-lysine, (1->1')-disulfide was then passed through a column of HP-20 resin (40 g). Sodium sulfate was removed by eluting the column with water (200 mL). The absence of sulfate in subsequent fractions was determined using a $BaCl_2$ test. The column was then eluted with 1:1 MeOH:water (300 mL). Finally the column was eluted with MeOH and fractions 3 to 8 (100 mL each) were pooled, concentrated and lyopholized to furnish $N^2$-[N-[(Phenylmethoxy) carbonyl]-L-homocysteinyl]-L-lysine, (1->1')-disulfide as a white powder (1.6 g). The overall yield beginning from Z-homocystine was 34%. Laboratory HPLC HI 91.

EXAMPLE 3

Aminotransferase Purification from *Sphingomonas paucimobilis* ATCC 202027 (Previously Identified as Pseudomonas SC 16113)

Fermentation process for growth of Sphingomonas ATCC 202027 was developed for the production of dipeptide aminotransferase. Dipeptide aminotransferase, an intracellularcellular enzyme used for the oxidation of $N^2$-[N-[(Phenylmethoxy)carbonyl]-L-homocysteinyl]-L-lysine, (1->1')-disulfide to [4S-(4α,7α,10aβ)]1-Octahydro-5-oxo-4-](phenylmethoxy) carbonyl]amino]-7H-pyrido-[2,1-b][1,3]thiazepine-7-carboxylic acid, discovered during screening of the Bristol-Myers Squibb culture collection and environmental isolates. The fermentation process was scaled-up to 500 L. The highest aminotransferase activity of 231 mg of [4S-(4α,7α,10aβ)]1-Octahydro-5-oxo-4-[(phenylmethoxy) carbonyl]amino]-7H-pyrido-[2,1-b][1,3]thiazepine-7-carboxylic acid, formed/hr/gram of protein was achieved after 48 hours growth period. Starting from the cell-extracts, the aminotransferase was purified 354 fold with a specific activity (mg product formed/hr/g of protein) of 36600. The purification procedure included DE-52 ion-exchange column chromatography, phenyl sepharose column chromatography and sephacryl S-200 column chromatography. The purified enzyme after sephacryl S-200 column chromatography showed a single protein band on SDS/PAGE using a silver stain. The molecular weight of enzyme as determined by gelfiltration techniques is 81,000 daltons and subunit size as determined SDS/PAGE is 40,000 daltons indicating that the dipeptide aminotransferase is a dimeric protein. The amino terminal and internal sequences of the purified protein were determined for cloning aminotransferase gene.

Growth of Pseudomonas sp. SC 16113 in Shake-flasks

One vial of organism was used to inoculate 100 ml of medium A containing 1.5% peptone, 0.01% yeast extract, 0.2% $KH_2PO_4$, 0.2% $K_2HPO_4$, 0.01% $MgSO_4$ and 0.2% NaCl. Cultures were grown at 28° C. and 280 RPM for 48 to 72 hours on a rotary shaker. One hundred mL of this culture was transferred to one liter of medium A. Cultures were grown in 4-L flask at 28° C. and 250 RPM for 48 hours on a rotary shaker. Cultures were harvested by centrifugation at 18,000×g for 15 minutes, cells were recovered and stored at −70° C. until used.

Preparation of Cell Extract

Preparation of cell extracts were carried out at 4–7° C. Cells were washed with 25 mM potassium phosphate buffer pH 8.0 (buffer A) and washed cells (2 g) were suspended in 10 mL of buffer A containing 10 mM Na-EDTA. To the cell suspensions, 0.1 mL of 100 mM PMSF solution in isopropanol and 0.1 mL of 0.5 M DTT were added. Cell-suspensions (20% W/V, wet cells) were passed through a French Press at 15,000 psi pressure and disintegrated cells were centrifuged at 25,000×g for 30 min at 4° C. The supernatant solution obtained after centrifugation is referred to as cell extracts. Cell suspensions of more than 100-ml volumes were disintegrated with a Microfluidizer (Microfluidics, Inc) at 12,000 psi (two passage) and disintegrated cells were centrifuged at 25,000×g for 30 min to obtain cell extracts.

Enzyme Assay

The reaction mixture in 5 mL contained 2.7 mL of cell extracts, 30 μL of 10 mM pyridoxal phosphate, 1.95 mL of dipeptide dimer solution (50 mg/mL stock solution), and 75 μL of sodium α-ketoglutarate (80 mg/mL stock solution). The reaction mixture was incubated at 30° C. at 100 RPM. At 1, 4 and 16 hours, 0.95 mL of samples were taken and 0.05 mL of TCA (100% w/v) was added. After one hour incubation with TCA at room temperature 1 mL of acetonitrile was added to the solution. Samples were analyzed for $N^2$-[N-[(Phenylmethoxy)carbonyl]-L-homocysteinyl]-L-lysine, (1->1')-disulfide and [[4S-(4α,7α,10aβ)]1-Octahydro-5-oxo-4-[(phenylmethoxy)carbonyl]amino]-7H-pyrido-[2,1-b][1,3]thiazepine-7-carboxylic acid, concentration by HPLC. Protein concentration in cell extract was determined by Bio-Rad protein reagent using bovine serum albumin as a standard. The assay mixture contained 1–10 μL of enzyme fraction, 0.8 mL water and 0.2 mL Bio-Rad reagent. After through mixing the absorbance of solution was measured at 595 nm. The concentration of protein was calculated from the standard graph derived with bovine serum albumin as standard protein.

Growth of *Sphinpomonas paucimobilis*. ATCC 202027 in a Fermentor

*Sphingomonas paucimobilis*. ATCC 202027 were grown in 700-L fermentors containing 500 L of medium A containing 1.5% peptone, 0.01% yeast extract, 0.2% $KH_2PO_4$, 0.2% $K_{2HPO4}$, 0.01% $MgSO_4$, 0.2% NaCl, 0.025% SAG and 0.025% Dow Corning antifoam. Growth consisted of two inoculum development stages and one fermentation stage. Inoculum development consisted of F1 and F2 stages. In the F1 stage, a frozen vial of *Sphingomonas paucimobilis*. ATOC 202027 was inoculated into 100 ml of medium B containing 1% glucose, 0.1% $KH_2PO_4$, 0.1% $K_{2HPO4}$, 0.05% $MgSO_4$, 0.05% yeast extract, 0.05% $(NH4)_2SO_4$, 0.05% NaCl, and 0.01% $CaCl_2$. The growth was carried out in 500-ml flasks at 28° C. and 250 RPM for 24 hours. In the F2 stage, 100-mL of F1 stage culture of organism was inoculated into 1 L of medium B in a 4-L flask and incubated at 28° C. and 250 RPM for 48 hours. Fermentor containing medium A was inoculated with 4 L of F2 stage inoculum and grown at 28° C. and 220 RPM agitation with 250 LPM (liter per minute) aeration and 10 PSIG back pressure. During fermentation, cells were periodically harvested by centrifugation from 200 ml of culture broth. Cell extracts were prepared as described earlier to assay for enzyme activity. The specific activity (mg of product formed/hr/g of protein) was determined.

HPLC Analysis for $N^2$-[N-[(Phenylmethoxy)carbonyl]-L-homocysteinyl]-L-lysine, (1->1')-disulfide and [4S-(4α,7α,10aβ)]1-Octahydro-5-oxo-4-[(phenylmethoxy)carbonyl]amino]-7H-pyrido-[2,1-b][1,3]thiazepine-7-carboxylic acid HPLC analysis was performed using a Hewlett-Packard (HP) 1090 with a Vydac C-18 reverse phase column. The mobile phase solvent A containing 0.1% trifluoroacetic acid (TFA) in water and solvent B containing 0.1% TFA in 70% acetonitrile: 30% water. The following gradient of solvent A and B was used for the separation of $N^2$-[N-[(Phenylmethoxy)carbonyl]-L-homocysteinyl]-L-lysine, (1->1')-disulfide and [4S-(4α,7α,10aβ)]1-Octahydro-5-oxo-4-[(phenylmethoxy)carbonyl]amino]-7H-pyrido-[2,1-b][1,3]thiazepine-7-carboxylic acid.

| | |
|---|---|
| 0 min | 100% A |
| 0–15 min | 50% B |
| 15–25 min | 100% B |
| 25–26 min | 0% B |
| 26–30 min | 0% B |

The flow rate was 1 mL/min. The column temperature was ambient, and the detection wavelength was 215 nm. Under this conditions, the retention times for $N^2$-[N-[(Phenylmethoxy)carbonyl]-L-homocysteinyl]-L-lysine, (1->1')-disulfide was 17.8 min and for [4S-(4α,7α,10aβ)]1-Octahydro-5-oxo-4-[(phenylmethoxy)carbonyl]amino]-7H-pyrido-[2,1-b][1,3]thiazepine-7-carboxylic acid was 20.1 min under above conditions. The retention times for monomer of $N^2$-[N-[(Phenylmethoxy)carbonyl]-L-homocysteinyl]-L-lysine, (1->1')-disulfide is 15.3 min.

Purification of Aminotransferase

Preparation of cell extracts were carried out at 4–7° C. Cells were washed with 25 mM potassium phosphate buffer pH 8.0 (buffer A) and washed cells (200 g) were suspended in 1L of buffer A containing 10 mM Na-EDTA. To the cell suspensions, 0.1 mL of 100 mM PMSF solution in isopropanol and 0.1 mL of 0.5 M DTT were added. Cell-suspensions (20% W/V, wet cells) were disintegrated with a Microfluidizer (Microfluidics, Inc) at 12,000 psi (two passage) and disintegrated cells were centrifuged at 25,000×g for 30 min to obtain cell extracts. The purification of aminotransferase was carried out by following steps.

(1) DEAE-cellulose Column Chromatography

The cell extract was loaded on to Whatman DE-52 column (400 mL packed bed) eqilibrated with buffer A. The column was washed with 400 mL of buffer A and then with 400 mL of buffer A containing 0.2 M NaCl. Enzyme activity was eluted with a 2L gradient of buffer A containing NaCl from 0.2–0.6 M. Fractions of 20 mL were collected. Fractions containing the highest specific activity were pooled.

(2) Phenyl Sepharose Column Chromatography

The pooled fraction from DE-52 column was adjusted to 1M ammonium sulfate (132 g/L ammonium sulfate added) and loaded on to Pharmacia fast flow Phenyl Sepharose column (150 mL bed volume) equilbrated with buffer A containing 132 g/L ammonium sulfate (1M ammonium sulfate). The column was washed with 150 mL of buffer A containing 1M ammonium sulfate and then with buffer A containing 0.25 M ammonium sulfate. The enzyme activity was eluted with a 400 mL gradient of buffer A containing ammonium sulfate from 0.25 M-0 M ammonium sulfate. Fractions of 20 mL were collected. The most active fractions were pooled and concentrated by ultrafiltration to 4 mL using an Amicon YM -10 membrane filtration.

[3] Sephacryl S-200 Column Chromatography

The concentrated fraction (4 mL) from Amicon step was loaded on to Sephacryl S-200 column (450 mL) equilibrated with buffer A. Fraction of 10 mL were collected.

Sodium Dodecyl Sulfate Polvacrylamide Gel-electrophoresis (SDS/PAGE)

The active fractions from Sephacryl S-200 column were evaluated by SDS-PAGE as described in the PhastSystem procedure by Pharmacia, using the homogeneous 12.5% Phastgel. The enzyme samples were added to a buffer containing 10 mM Tris-HCl, 1 mM EDTA (ethylenediamine tetraacetic acid) pH 8, 2.5% SDS and 5% β-mercaptoethanol. The mixture was heated at 100° C. for 5 minutes, and bromophenol blue was added to 0.01%. Gels were stained with silver stain and destained in 10% acetic acid solution. Marker with standard molecular weight contained phosphorylase β(94,000), bovine serum albumin (67, 000), ovalbumin (43,000), cabonic anhydrase (30,000), soybean trypsin inhibitor (20,100), α-lactabumin (14,400).

Determination of Molecular Weight of Aminotransferase

The molecular weight of aminotransferase was determined by Pharmacia size exclusion chromatography using a Superose-12 column (15 cm×1 cm). The column was equilibrated with buffer A. The Aminotransferase (Sephacryl S-200 fraction) was applied to the column and eluted with the buffer A at a flow rate of 0.4 mL/min. Fractions of 1 mL were collected. Standard protein mixture containing thryglobulin (669,000 MW), ferritin (440,000 MW), Human IgG (150,000 MW), human transferrin (81,000 MW), Ovalbumin (43,000 MW), Myoglobin (17,600 MW), and Vitamin B12 (1355 MW) was also applied to the column and eluted with buffer C. Molecular weight of glutamate oxidase was determined from standard graph.

Aminotransferase activity from cell extracts of Pseudomonas sp. SC 16113 grown in shake-flask cultures were 0.2 mg of product [4S-(4I,7I, 10aJ)]1-Octahydro-5-oxo-4-[(phenylmethoxy)carbonyl]aminol-7H-pyrido-[2,1-b][1,3]thiazepine-7-carboxylic acid, methyl ester formed/hr/ mL of extract. All activity was obtained in the cells after centrifugation of culture broth indicated that the enzyme is intracellular protein.

Aminotransferase was purified from cell extracts of *Sphingomonas paucimobilis* ATCC 202027 (Table 1)

The purified protein (CM cellulose fraction 17 & 18) gave a single band of protein on a SDS/PAGE corresponding to a molecular weight of 40,000 daltons. The molecular weight of purified protein was determined by gel-filtration on a Superose-12 column and FPLC system. The molecular weight of purified protein is 81000 daltons indicating that dipeptide aminotransferase is a dimeric protein.

The aminoterminal and internal sequence of purified dipeptide aminotransferase was determined to synthesize oligonucleotide probes for further cloning of enzyme.

TABLE 1

| Step | Volume (mL) | Total Protein (mgs) | Total Activity (Units) | Sp. Activity (Units/mgs) | Purification (fold) |
|---|---|---|---|---|---|
| Cell extract | 800 | 2544 | 400 | 157 | 1 |
| DE-52 | 150 | 57.3 | 219 | 1462 | 9.3 |
| Phenyl-sepharose | 120 | 5.04 | 93 | 18476 | 117 |
| Sephacryl S-200 | 40 | 1.32 | 53 | 3666 | 254 |

EXAMPLE 4

Production of [4S-(4I,7I,10aJ)]1-Octahydro-5-oxo-4-[(phenylmethoxy)carbonyl]amino]-7H-pyrido-[2,1-b](1,3]thiazepine-7-carboxylic acid, from $N^2$-[N-[(Phenylmethoxy)carbonyl]-L-homocysteinyl]-L-lysine, (1->1')-disulfide using Aminotransferase from Pseudomonas sp. SC 16113(*Sphingomonas paucimobilis* ATCC 202027)

Reaction:

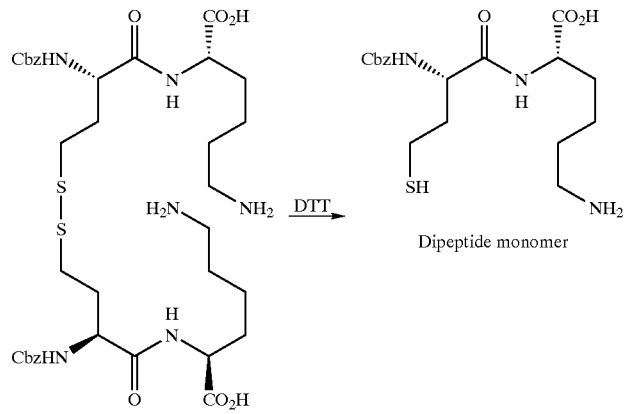
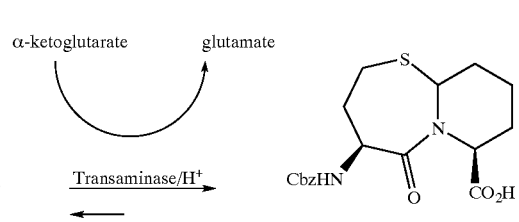

Dipeptide monomer

Preparation of Cell-free Extracts

Approximately 700 g of Pseudomonas sp. SC 16113 cells (XP9540; Rec 50; Tank 122) were suspended in 3.5 L 0.01M phophate buffer, pH 8; 5 mM EDTA and homogenized with a Tekmar laboratory homogenizer. These cells were then centrifuged at 4° C. for 30 min at 12000 rpm. The supernatent was then discarded. The cells were resuspended in 3.5 L 0.1M phophate buffer, pH 8; containing 5 mM DTT, 1 mM PMSF, and 5 mM EDTA. The homogenized cell-suspensions were then passed twice through Microfluidzer (200 m chamber) at 7500 psi to prepare the cell-free extracts. The chamber and the cell-suspensions were chilled to 4° C. prior to the cell disruption. The cell extract was then centrifuged to remove the debri (4° C., 13000 rpm, 3 hour).

Reaction Conditions

To the 2 L of cell-free extracts, 10 ml each of 10 mM pyridoxal phosphate, α-ketoglutarate (80 mg/ml) and NAD (20 mg/ml) were added. The reaction mixture was mixed gently with an overhead teflon agitator (200 rpm). To the stirring reaction mixture, 120 ml of $N^2$-[N-[(Phenylmethoxy)carbonyl]-L-homocysteinyl]-L-lysine, (1->1')-disulfide solution (50 mg/ml) was added. The reaction was carried out at ambient temperature. Aliquots were taken out every 0.5 hrs to measure the amount of [4S-(4α,7α,10aβ)]1-Octahydro-5-oxo-4-[(phenylmethoxy)carbonyl] amino]-7H-pyrido-[2,1-b][1,3]thiazepine-7-carboxylic acid formed. After 1.75 hours of reaction, 200 ml of TCA solution (100% v/v) was added, and after mixing the pH of the resulting solution was 3.1. To the reaction mixture 1.8 L of acetonitrile was added mixed gently for 15 minutes, then let stand at room temperature for 2.30 hours. The quenched reaction mixture was then centrifuged to remove precipitated proteins at 4° C. at 13000 rpm for 1 hr. The aqueous/organic supernate was used for isolation of product [4S-(4I, 7I,10aJ)]1-Octahydro-5-oxo-4-[(phenylmethoxy) carbonyl] amino]-7H-pyrido-[2,1-b][1,3]thiazepine-7-carboxylic acid. About 40M % yield of product was obtained.

EXAMPLE 5

Cloning and Expression of Aminotransferase from *Sphinglomonas paucimobilis* ATCC 202027 in to *Escherichia coli*

Amplification of a PCR fragment corresponding to the *Sphingomonas paucimobilis* ATCC 202027 aminotransferase gene The lysine aminotransferase protein (LAT) was found to convert $N^2$-[N-[(Phenylmethoxy)carbonyl]-L-homocysteinyl]L-lysine, (1->1')-disulfide to (6). The lysine aminotransferase protein (LAT) was purified from *Sphingomonas paucimobilis* ATCC 202027 and its amino terminal and internal peptide sequences were determined. A mixed oligonucleotide based on the amino terminal sequence was synthesized taking into consideration the high G+C content of the *Sphingomonas paucimobilis* ATCC 202027 genome.

| Ile | Thr | Pro | Leu | Met | Pro | Val | Tyr |
|---|---|---|---|---|---|---|---|
| ATC/T | ACC/G | CCG | C/TTG | ATG | CCG | GTC/G | TAT |

The DNA sequence is SEQ.ID.NO.:3 and the amino acid sequence is SEQ.ID.NO.:4

The downstream (antisense) primer based on a conserved amino acid sequence found in other aminotransferases was (Tyr-Gly-Asn-Pro-Leu-Ala)(SEQ.ID. NO.:5), with a corresponding oligomer of GCG/C AGC/G GGG TTC/G CCC/G CC (antisense) (SEQ.ID.NO.:6). A PCR reaction using Tth polymerase was performed to obtain a 850 base pair (bp) fragment. This fragment was isolated and cloned into plasmid vector pCRII. The presence of the insert was verified using PCR and restriction digests, and the sequence of the insert was determined using an ALFexpress automated DNA sequencer. This sequence demonstrated strong homology to bacterial aminotransferases found in GenBank database. An internal peptide sequence of 19 amino acids obtained from a tryptic peptide of purified aminotransferase protein from *Sphingomonas paucimobilis* ATCC 202027 was also located. These data indicated that the PCR fragment amplified was in fact representative of part of the bona fide LAT enzyme.

Isolation of the Complete lat Gene

The 850-bp PCR fragment was used as a hybridization probe to identify the entire LAT gene. *Sphingomonas paucimobilis* ATCC 202027 chromosomal DNA was purified and partially digested with restriction endonuclease Sau3A1.

Fragments of 6–10 kilobases (kb) were extracted from an agarose gel following electrophoresis and ligated to BamHI-cleaved plasmid vector pZeroI. The DNA was transformed into *E. coli* TOP 10 F' cells by electroporation and selected on LB medium containing the antibiotic Zeocin. Transformants were then transferred onto nylon filters and lysed in situ. Following hybridization using a $^{32}$P-labeled PCR fragment, several strongly hybridizing colonies were seen. They were picked from the master plate and grown in liquid medium for plasmid DNA isolation. To confirm that these plasmids did in fact contain the lat gene, two criteria were used: (1) The DNA must possess a 669-bp internal NcoI fragment which is found in the PCR fragment and (2) the DNA must serve as a template for amplification using primers specific to the 850-bp PCR fragment. One colony contained a plasmid which met both these criteria. It contained an insert of approximately 6.3 kb and was thus named pLAT6.3.

Sequencing of the Complete lat Gene

The entire aminotransferase gene of pLAT6.3 was sequenced (FIG. 1). A typical gram-negative promoter and ribosome binding site followed 9 bases later by an initiation codon ATG (Methionine) was found. The size of the coding region of the gene is 1221 bp. Based on our computer analysis of the gene, this region should encode 398 amino acids with a molecular weight of 42,457 daltons. We identified additional runs of amino acids which matched that obtained from internal peptide sequencing of the purified LAT protein. This information confirmed that the entire lat gene was present on pLAT6.3 and that it encoded the same protein isolated from *Sphingomonas paucimobilis* ATCC 202027.

Cloning and Overexpression of the lat Gene in *E. coli*

The polymerase chain reaction was used to precisely amplify the lat gene which also contained restriction sites at both ends for cloning into expression plasmids. For digestion and ligation into pKK223-3, the lat gene was amplified with EcoRI and BamHI sites at the 5' and 3' ends. Similarly, NdeI and XbaI sites were added to the 5' and 3' ends respectively for ligation into pAL781. Both the amplified fragment and the vector DNAs were cleaved with the appropriate enzymes and ligated together. The plasmids formed were named pkk 223-3-LAT and pAL781-LAT/A respectively. The ligation samples were electroporated into *E. coli* strains TOP 10 F' (pKK223-3-LAT) or GI724 (pAL781-LAT/A). The presence of the lat gene in the recombinant plasmids was confirmed using PCR with lat-specific primer and restriction digestion analysis.

TOP 10 F'(pKK223-3-LAT) was grown in LB medium (tryptone, 1.0%; yeast extract, 0.5%; NaCl, 1.0%) containing 100 Tg/ml of ampicillin. At an OD600 of ca. 1.0, the tac promoter controlling expression was induced with 100 TM IPTG. Samples were taken 1, 2, and 3 hr post-induction and analyzed for aminotransferase activity and used in the bioconversion of $N^2$-[N-[(Phenylmethoxy)carbonyl]-L-homocysteinyl]-L-lysine, (1->1')-disulfide to [4S-(4I,7I,10aJ)]1-Octahydro-5-oxo-4-[(phenylmethoxy)carbonyl] amino]-7H-pyrido-[2,1-b][1,3]thiazepine-7-carboxylic acid, (table 2).

GI724(pAL781-LAT/A) was grown for 18–20 hr in MRM (0.6% $Na_2HPO_4$, 0.3% $KH_2PO_4$, 0.125% $(NH_4)_2SO_4$, 2% Casamino acids [Bacto grade], 1.0% glycerol, 1 mM MgSO4). The culture was then inoculated into MIM medium at a starting $OD_{600}$ of 0.20 (MIM contained 0.6% $Na_2HPO_4$, 0.3% $KH_2PO_4$, 0.125% $(NH_4)_2SO_4$, 0.2% Casamino acids [Bacto grade], 0.5% glucose, and 1 mM MgSO4). Ampicillin was added to all media at a final concentration of 100 Tg/ml. At an $OD_{600}$ of ca. 0.5, L-tryptophan from a filter-sterilized 10 mg/ml solution was added to a final concentration of 100 Tg/ml. Samples were removed at 3, 6, and 22 hr post-induction for aminotransferase activity and used in the bioconversion of $N^2$-[N-[(Phenylmethoxy)carbonyl]-L-homocysteinyl]-L-lysine, (1->1')-disulfide to [4S-(4α,7α,10aβ)]1-Octahydro-5-oxo-4-[(phenylmethoxy)carbonyl]amino]-7H-pyrido-[2,1-b][1,3]thiazepine-7-carboxylic acid.

Both recombinant strains were able to convert $N^2$-[N-[(Phenylmethoxy)carbonyl]-L-homocysteinyl]-L-lysine, (1->1')-disulfide to [4S-(4α,7α,10aβ)]1-Octahydro-5-oxo-4-[(phenylmethoxy)carbonyl]amino]-7H-pyrido-[2,1-b][1,3]thiazepine-7-carboxylic acid (Table 2), while control culture which did not possess the lat gene showed no such activity. Expression using the tryptophan-inducible promoter was better than that using the tac promoter so the former strain was investigated in more detail. Activity was seen at all time points but peaked at 6 hr post-induction (Table 2). Coincidentally, extracts prepared from the induced culture revealed a strong protein band of the same molecular weight as the purified aminotransferase at 6 hr post-induction. Further experiments indicated that most of this protein was in the intracellular soluble fraction.

A kanamycin-resistant version of the above plasmid was also created. Plasmid pET9b was excised by digestion with restriction endonucleases AlwNI and EcoRI. A 1171-bp fragment containing the Kanamycin resistant ($Km^R$) gene was purified and the ends made blunt-ended by treatment with Klenow DNA polymerase plus all four deoxyribonucleotides. The modified fragment was ligated into pAL781-LAT/A which had been digested with SspI. After electroporation into GI724, kanamycin-resistant colonies were picked and verified for the presence of both the $Kn^R$ and lat genes. This plasmid was named pAL781-LAT/AK. A fermentation identical to the one performed for the ampicillin-resistant version of the plasmid was carried out. Assay results as shown in the Table 2.

TABLE 2

| Sample | Culture Growth (hours) | Compound B formed (mg/mL) | Wet Cells Weight (mgs) |
|---|---|---|---|
| TOP 10 F'(pKK223-3-LAT) | 3 | 0.126 | 157 |
| GI724(pAL781-LAT/A) | 6 | 0.422 | 250 |
| GI724(pAL781-LAT/A) | 2 | 0.195 | 420 |
|  | 4 | 0.266 | 340 |
|  | 6 | 0.308 | 300 |
| GI724(pAL78I-LAT/AK) | 2 | 0.193 | 330 |
|  | 4 | 0.311 | 300 |
|  | 6 | 0.292 | 390 |
| Contol (without lat gene) | 6 | 0 | 70 |

**Compound B is [4S-(4I, 7I, 10aJ)]1-Octahydro-5-oxo-4-[(phenylmethoxy) carbonyl]amino]-7H-pyrido-[2,1-b][1,3]thiazepine-7-carboxylic acid,

EXAMPLE 6

Production of Aminotransferase (Cloned from *Sphingomonas paucimobilis* ATCC 202027 in to *Escherichia coli* GI724 (pAL781-LAT)

The process described is for the growth of *E. coli* GI724 (pAL781-LAT) in 20 liter fermentors. The *E. coli* cells produce an aminotransferase enzyme which is used for the enzymic conversion of $N^2$-[N-[(Phenylmethoxy)carbonyl]-L-homocysteinyl]-L-lysine, (1->1')-disulfide to [4S-(4α,7α,10aβ)]1-Octahydro-5-oxo-4-[(phenylmethoxy)carbonyl]amino]-7H-pyrido-[2,1-b][1,3]thiazepine-7-carboxylic acid.

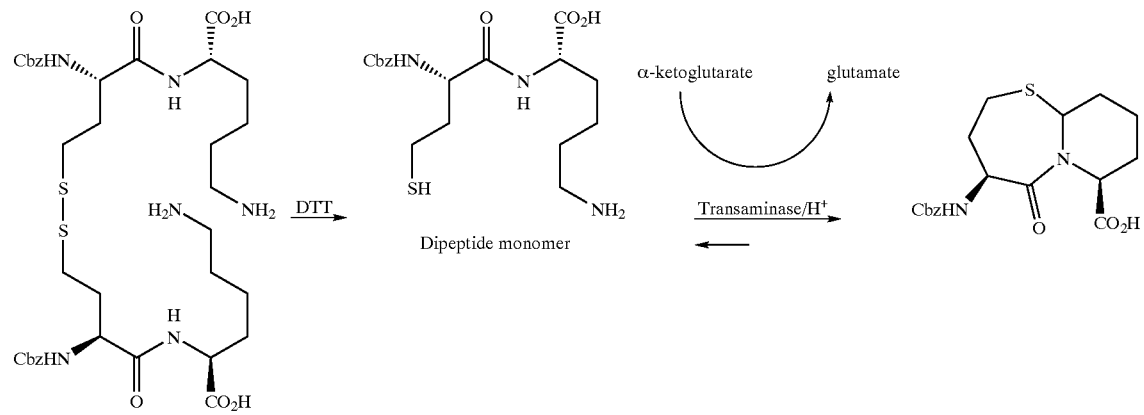

Dipeptide monomer

The aminotransferase enzyme is produced intracellularly. The recovered cell paste can be used to prepare a cell-free extract for the biotransformation.

Process Details for Growth of *Escherichia coli*

*E. coli* cultures were first grown in a 4-L flask containing 1-L medium for 24 hours and 24-hours grown cultures were inoculated into 25-L fermentor containing 16 L medium. Medium composition and growth conditions are as follows:

The strain approved for all fermentations is *E. coli* GI724 (pAL781-LAT/A). A kanamycin-resistant derivative of pAL781-LAT that also overexpresses the enzyme in *E. coli* GI724 is available and is being tested at the 16-liter scale.

Stage One—F1 Stage

1. Two 1 ml vials are inoculated into each 4 liter flask (two are needed for a 16 liter fermentor) containing 1 liter of MT3 medium. Each flask is incubated at 30° C. for 24 hours at 250 RPM.

| MT3 medium: | |
|---|---|
| 1.0% | NZ Amine A |
| 2.0% | Yeastamine |
| 2.0% | Glycerol |
| 0.6% | Sodium Phosphate dibasic |
| 0.3% | Potassium Phosphate monobasic |
| 0.125% | Ammonium sulfate |
| 0.0246% | Magnesium sulfate heptahydrate |
| 0.01% | Ampicillin, sodium salt |

Batched with deionized water and autoclaved for 20 minutes at 121° C.

Stage Two—Fermentation Stage

Medium in the fermentor is batched with deionized water to a final volume of 15 liters with the following ingredients:

| 1.0% | NZ Amine A |
|---|---|
| 2.0% | Yeastamin |
| 2.0% | Glycerol |
| 0.6% | Sodium Phosphate dibasic |
| 0.3% | Potassium Phosphate monobasic |
| 0.125% | Ammonium sulfate |
| 0.05% | Polypropylene glycol |

The pH after batching is adjusted to 7.0–7.2. Sterilization is conducted at 121.5° C. for 20 minutes by jacket steam only. After sterilization, the temperature is reduced to 37° C. and the volume is approximately 16 liters. Prior to inoculation, a solution containing magnesium sulfate and ampicillin are added aseptically (after filter sterilization) to the tank to a final concentration of 1 mM and 100 mg/L, respectively. The fermentor is inoculated with broth from 1 or more F1 flasks to yield an equivalent optical density in the tank of 0.25 at Log 0. Approximately, 1.5 liters of inoculum (1½ F1 flasks) will be needed for a 16 liter working volume fermentor. Note, all filter sterilization of medium components is done with a 0.2 micron cellulose nitrate filter. Optical density is measured with a spectrophotometer.

Fermentor Operating Parameters 16 liter working volume
Temperature: 37° C.
Aeration: 0.5 volume air per working volume per minute
Pressure: 690 mBar
Agitation: 250 RPM There is no pH control and foam is controlled by addition of UCON on demand.

Samples are taken during the course of the fermentation for pH, partial volume of solids, relative viscosity, optical density, wet cell weights and enzyme activity. The optical density of properly diluted (with log M medium) samples is measured at 600 nm on a spectrophotometer which has been blanked with log M medium. Off gas $CO_2$ from the fermentor is monitored continuously with a gas analyzer. The fermentor runs for 6–8 hours. At that time the tank is subcooled to 10° C. while maintaining the same agitation and aeration (in overlay) and then recovered by centrifugation.

Yields and Purities

Four batches of *E. coli* have been run based on this Preliminary Laboratory Process Description. The results of these batches are summarized below.

| Batch No. | XP9682 | XP9683 | XP9683 | XP9683 |
|---|---|---|---|---|
| Tank No. | BF#3 | BF#3 | BF#4 | BF#5 |
| Fermentor Volume (L) | 20 | 20 | 20 | 20 |
| Working Volume (L) | 16 | 16 | 16 | 16 |
| Harvest Log (hr) | 6 | 6 | 8 | 6 |
| Aminotransferase Activity [90 min. assay] (mg product/g wet cell/hr) | 1.01 [70 min. assay] | 1.01 | 1.67 | 1.67 |
| Harvested Wet Cell Weight (g/L) | 9.1 | 8.9 | 8.8 | 9.4 |

Preparation of Cell-free Extracts 15 g of centrifuged wet cell paste were suspended in 100 ml of 100 mM phosphate buffer pH 8.0, 10 mM Na EDTA and homogenous cell suspensions were using a homogenizer. To the cell suspensions 0.1 ml of 0.1 M PMSF solution in isopropanol and 0.1 ml of 0.5 M DTT solution were added. Cell suspensions were passed through a French Press at 15,000 PSI pressure and disintegrated cells were centrifuged at 25,000×g at 4° C. The supernatant solution obtained after centrifugation is referred to as cell extracts. Cell suspensions of more than 100 mL volumes were disintegrated with a Microfluidizer at 12, 000 PSI pressure (two passage) and disintegrated cells were centrifuged at 25,000×g for 30 min to obtain cell extracts.

Enzyme Assay

The reaction mixture in 1 mL contained 0.1 mL of cell-free extracts, 0.8 ml of 100 mM phosphate buffer pH 8.0 containing 10 mM Na EDTA, 10 μl of 0.5 M DTT solution, 10 μl of 10 mM PLP solution, 25 μl of α-ketoglutarate solution and 0.65 μl of 50 mg/mL of dipeptide dimer solution. Reaction mixtures were prepared in tubes. Tubes were incubated at room temperature on a end-over-end shaker. Samples were taken at 0.5, 1.5 and 6 hours. Quench the enzyme reaction mixture by adding 0.2 ml of trichloroacetic acid and 1.8 ml of acetonitrile to the reaction mixtures. Let mixture stand at room temperature for 2–4 hours and analyzed by HPLC for substrate and product concentration as follows:

Analytical Methods

Filter the quenched reaction mixture to a HPLC vial, using a Lid/X type syringe filter. The concentration of substrate and product are determined by the following HPLC method.

| Column | Vydac C-18 |
|---|---|
| Buffers | A: 0.1% TFA in $H_2O$ |
| | B: 0.1% TFA in 70% Acetonitrile, 30% $H_2O$ |
| Gradient | 0–15 min: 50% B |
| | 15–25 min: 100% B |
| | 25–26 min: 0% B |
| | 26–30 min: 0% B |
| Flow Rate | 1 ml/min. |
| Detector | UV-215 nm. |

The dimer ($N^2$-[N-[(Phenylmethoxy)carbonyl]-L-homocysteinyl]-L-lysine, (1->1')-disulfide) elutes at 15.3 min and the product (6) elutes at 20.1 min under these conditions.

Determination of Protein Content of the Cell-free Extracts

Bio-Rad protein assay was used for determining the protein quatitation. The assay was carried out as described by the manufacturer (Bio-Rad). The assay consists of adding 5 μL of cell-free extract in a total volume of 0.8 mL water. The Bio-Rad reagent (0.2 mL) is added to the 0.8 mL and after thorough mixing the absorbance of the solution was measured at 595 nm. The concentration of the protein was read from the standard curve with bovine serum albumin (BSA) as the standard protein.

Unit of activity=μmoles of product formed/min/per mL of cell extracts.

EXAMPLE 7

Preparation of [4S-(4I,7I,10aJ)]1-Octahydro-5-oxo-4-[(phenylmethoxy) carbonyl]amino]-7H-pyrido-[2,1-b][1,3]thiazepine-7-carboxylic acid, from $N^2$-[N-[(Phenylmethoxy)carbonyl]-L-homocysteinyl]-L-lysine, (1->1')-disulfide Introduction The process described is the conversion of $N^2$-[N-[(Phenylmethoxy)carbonyl]-L-homocysteinyl]-L-lysine, (1->1')-disulfide to [4S-(4α,7α,10aβ)]1-Octahydro-5-oxo-4-[(phenylmethoxy)carbonyl]amino]-7H-pyrido-[2,1-b][1,3]thiazepine-7-carboxylic acid, by oxidative deamination using cloned transaminase from *Sphingomonas paucimobilis* (previously identified as Pseudomonas sp) SC 16113 expressed in *E. coli* GI724[paI781-LAT]SC16240. The reaction requires α-ketoglutarate, as the amine acceptor. DTT is used to reduce the dimer $N^2$-[N-[(Phenylmethoxy) carbonyl]-L-homocysteinyl]-L-lysine, (1->1')-disulfide to monomer. Glutamate produced during the reaction is recycled to α-ketoglutarate by the oxidative deamination using glutamate oxidase from Streptomyces sp. obtained from Sigma Chemicals, St. Louis, Mo. (Product #G0400). The expected reaction molar yield is 70–80 M %. The procedure described uses cell-free extracts for transaminase, and glutamate oxidase.

| Raw Materials for 22.2 g Batch: | | | |
|---|---|---|---|
| Material | Source | Mol. Wt. | Amount |
| (4) | 38449-156-29 | 794.11 | 22.2 g |
| α-Ketoglutarate | Sigma | 63.06 | 19.5 g |
| Pyridoxal phosphate | Sigma | 247.1 | 100 mg |
| Dithiothreitol | Sigma | 154.2 | 7.03 g |
| $K_2HPO_4$ | Fisher | 174.2 | 16.1 g |
| $KH_2PO_4$ | Fisher | 136.14 | 16.1 g |
| EDTA | Sigma | 292.2 | 3.65 g |
| PMSF | Sigma | 174.2 | 87 mg |

-continued

| Raw Materials for 22.2 g Batch: | | | |
|---|---|---|---|
| Material | Source | Mol. Wt. | Amount |
| Trichloroacetic acid (TCA) | Sigma | 114 | 600 mL |
| NaOH | Fisher | 40 | |
| Acetonitrile | VWR | 41.05 | 5 L |
| Transaminase from E. coli GI 724 [pAL781-LAT] (SC16240) | | | 200 Units Cell extract |
| Glutamate oxidase from Streptomyces sp. (Sigma Chemicals) | | | 8150 Units (partially purified) |
| Water, deionized | | | 4.5 L |

Process Details

The process details for the reaction steps based on 22 g $N^2$-[N-[(Phenylmethoxy)carbonyl]-L-homocysteinyl]-L-lysine, (1->1')-disulfide input.

(1) Transaminase
Preparation of Cell-free Extracts 75 g of wet recombinant E. coli cells GI 724[pAL781-LAT] (SC16240) (XP9676; Rec126) were suspended in 500 mL of 0.1 M phosphate buffer, pH 7.8 containing 5 mM DTT, 1 mM PMSF, and 5 mM EDTA in a 1 L beaker. Cell-suspensions were homogenized with a Tekmar laboratory homogenizer. Cell-suspensions were passed twice through Microfluidzer at 7500 psi and 4° C. Disrupted cell-suspensions were centrifuged at 4° C. at 13000 rpm for 25 min. to remove the debris.

(2) Reaction Conditions 22.2 g of $N^2$-[N-[(Phenylmethoxy)carbonyl]-L-homocysteinyl]-L-lysine, (1->1')-disulfide into a 5 L bioreactor. 2.5 L of phosphate buffer pH 7.8 containing 10 mM EDTA to the bioreactor. The reaction mixture was agitated at 200 rpm. Gradually increase the pH of the above solution to 12.0 by slow addition of 5N NaOH, while stirring the solution at room temperature. Maintained the pH at 12.0 with the addition of 5N NaOH, until all solid was dissolved. The pH was readjusted to 7.8 with slow addition of conc. $H_3PO_4$. The temperature of the reaction mixture was maintained at 30° C. with a water bath. To the reaction mixture, 6.75 g of DTT, 19.5 g of α-ketoglutarate, disodium salt and 100 mg of pyridoxal phosphate were added. Additional 1.4 L of 100 mM phosphate buffer, pH 7.8 containing 10 mM EDTA was added to the reaction mixture. The reaction was started by the addition of 100 mL of cell-extracts of transaminase [aminotransferase (1 unit/mL activity) from Escherichia coli]. 300 mL of Glutamate oxidase solution (7 U/mL) was added at 30 minutes, 1 hr, 1.5 hrs, and 3.5 hrs. The pH was maintained at 7.8 with the addition of 5N NaOH. Periodically samples of 1 mL were removed and quenched with 0.1 mL of trichloroacetic acid and 0.9 mL of acetonitrile. The sample was allowed to stand at room temperature for 2 h, then filtered and analyzed by HPLC to measure the amount of [4S-(4α,7α,10aβ)]1-Octahydro-5-oxo-4-[(phenylmethoxy)carbonyl]amino]-7H-pyrido-[2,1-b][1,3]thiazepine-7-carboxylic acid, formed. After 6 hours of reaction time, 0.6 L of TCA solution (100% v/v) was added to the reactor to terminate the enzymatic reaction. The solution was mixed for 15 minutes, and let stand at room temperature for 3 hrs. To the reaction, 5L of acetonitrile was added and the amount of product formed was then obtained by an HPLC quantiation of an aliquot.

| | Yields | | | |
|---|---|---|---|---|
| Experiment # | Input (g) | Compound A* (g) | Compound B** (g) | Yield (M %) |
| 40455-23 | 0.30 | 0.07 | 0.19 | 64.2 |
| 40455-24 | 3.00 | 0.83 | 1.90 | 66.5 |
| 40455-41 | 5.00 | 1.35 | 2.92 | 65.0 |
| 40455-43 | 12.20 | 4.30 | 8.00 | 71.0 |
| 40437-28-15 | 22.50 | 4.70 | 15.5 | 70.0 |

*Compound A is $N^2$-[N-[(Phenylmethoxy)carbonyl]-L-homocysteinyl]-L-lysine, (1 ->1')-disulfide
**Compound B is [4S-(4α, 7β, 10aβ)]1-Octahydro-5-oxo-4-[(phenylmethoxy)carbonyl]amino]-7H-pyrido-[2,1-b][1,3]thiazepine-7-carboxylic acid.

Enzymatic conversion of $N^2$-[N-[(Phenylmethoxy)carbonyl]-L-homocysteinyl]-L-lysine, (1->1')-disulfide to [4S-(4α,7α,10aβ)]1-Octahydro-5-oxo-4-[(phenylmethoxy)carbonyl]amino]-7H-pyrido-[2,1-b][1,3]thiazepine-7-carboxylic acid was carried out using transaminase from rE. coli. The amino-acceptor α-ketoglutarate, was regenerated using partially purified glutamate oxidase from Streptomyces sp. obtained from Sigma Chemicals Co., St. Louis, Mo. (Product #G0400). The reaction was carried out with 3.0 g and 5.0 g of $N^2$-[N-[(Phenylmethoxy)carbonyl]-L-homocysteinyl]-L-lysine, (1->1')-disulfide in 1 L of 100 mM phosphate buffer. Glutamate oxidase (570 units) was added periodically at 30, 60, and 210 min. After 300 min of reaction time, >66 M % yield was observed. The mass-balance was >95%.

In small scale reactions, (0.1 L) the input of $N^2$-[N-[(Phenylmethoxy)carbonyl]-L-homocysteinyl]-L-lysine, (1->1')-disulfide was increased to 5 g/L. Using standard bioconversion conditions, the yield of [4S-(4α,7α,10aβ)]1-Octahydro-5-oxo-4-[(phenylmethoxy)carbonyl]amino]-7H-pyrido-[2,1-b][1,3]thiazepine-7-carboxylic acid, was observed to be >70%.

The preparative scale enzymatic conversion of $N^2$-[N-[(Phenylmethoxy)carbonyl]-L-homocysteinyl]-L-lysine, (1->1')-disulfide (5 g/L) to [4S-(4α,7α,10aβ)]1-Octahydro-5-oxo-4-[(phenylmethoxy)carbonyl]amino]-7H-pyrido-[2,1-b][1,3]thiazepine-7-carboxylic acid, was conducted in 2.5 L volume using transaminase from rE. coli and glutamate oxidase from Sigma Chemicals Co. The input of $N^2$-[N-[(Phenylmethoxy)carbonyl]-L-homocysteinyl]-L-lysine, (1->1')-disulfide was 12.2 g. Using standard bioconversion conditions, 7.0 g of [4S-(4α,7α,10aβ)]1-Octahydro-5-oxo-4-[(phenylmethoxy)carbonyl]amino]-7H-pyrido-[2,1-b][1,3]thiazepine-7-carboxylic acid, was prepared. The yield was 11 M %.

A second preparative scale enzymatic conversion of $N^2$-[N-[(Phenylmethoxy)carbonyl]-L-homocysteinyl]-L-lysine, (1->1')-disulfide (5 g/L) to [[4S-(4α,7α,10aβ)]1-Octahydro-5-oxo-4-[(phenylmethoxy) carbonyl]amino]-7H-pyrido-[2,1-b][1,3]thiazepine-7-carboxylic acid, was conducted in 4 L volume using transaminase from rE. coli and glutamate oxidase from Sigma Chemicals Co. The input of $N^2$-[N-[(Phenylmethoxy)carbonyl]-L-homocysteinyl]-L-lysine, (1->1')-disulfide was 22.2 g. Using standard bioconversion conditions, 14.4 g of [4S-(4α, 7α, 10aβ)]1-Octahydro-5-oxo-4-[(phenylmethoxy)carbonyl]amino]-7H-pyrido-[2,1-b][1,3]thiazepine-7-carboxylic acid, was prepared. The yield was 67 M %.

EXAMPLE 7a

Preparation of [4S-(4α,7α,10aβ)]1-Octahydro-5-oxo-4-[(phenylmethoxy) carbonyl]amino]-7H-pyrido-[2,-1-b][1,3]thiazepine-7-carboxylic acid, from N²-[N-[(Phenylmethoxy)carbonyl]-L-homocysteinyl]-L-lysine, (1->1')-disulfide Reaction in the Absence of Glutamate Oxidase The process described is the conversion of N²-[N-[(Phenylmethoxy)carbonyl]]-L-homocysteinyl]-L-lysine, (1->1')-disulfide to [4S-(4α,7α,10aβ)]1-Octahydro-5-oxo-4-](phenylmethoxy)carbonyl]amino]-7H-pyrido-[2,1-b][1,3]thiapezine-7-carboxylic acid by oxidative deamination using cloned transaminase from *Sphingomonas paucimobilis* (previously identified as Pseudomonas sp) SC16113 expressed in *E. coli* GI724[pAL781-LAT]SC16240. The reaction requires α-ketoglutarate, as the amine acceptor. DTT is used to reduce the dimer N²-[N-[(Phenylmethoxy)carbonyl]-L-homocysteinyl]-L-lysine, (1->1')-disulfide to monomer.

Raw Materials for 22.2 Batch:

| Material | Source | Mol. Wt. | Amount |
|---|---|---|---|
| (4) | 38449-156-29 | 794.11 | 22.2 g |
| α-Ketoglutarate | Sigma | 63.06 | 19.5 g |
| Pyridoxal phosphate | Sigma | 247.1 | 100 mg |
| Dithiothreitol | Sigma | 154.2 | 7.03 g |
| K₂HPO₄ | Fisher | 174.2 | 16.1 g |
| KH₂PO₄ | Fisher | 136.14 | 16.1 g |
| EDTA | Sigma | 292.2 | 3.65 g |
| PMSF | Sigma | 174.2 | 87 mg |
| Trichloroacetic acid (TCA) | Sigma | 114 | 600 mL |
| NaOH | Fisher | 40 | |
| Acetonitrile | VWR | 41.05 | 5 L |
| Transaminase from *E. coli* GI 724 [pAL781-LAT] (SC16240) | | | 200 Units Cell extract |
| Water, deionized | | | 4.5 L |

Process Detail 22.2 g of N²-[N-[(Phenylmethoxy)carbonyl]-L-homocysteinyl]-L-lysine, (1->1')-disulfide into a 5 L bioreactor, 2.5 L of phosphate buffer pH 7.8 containing 10 mM EDTA to the bioreactor. The reaction misture was agitated at 200 rpm. Gradually increase the pH of the above solution to 12.0 by slow addition of 5N NaOH, while stirring the solution at room temperature. Maintained the pH at 12.0 with the addition of 5N NaOH, until all solid was dissolved. The pH was readjusted to 7.8 with slow addition of conc. H₃PO₄. The temperature of the reaction mixture was maintained at 30° C. with a water bath. To the reaction mixture, 6.75 g of DTT, 195 g of α-ketoglutarate, disodium salt and 100 mg of pyridoxal phosphate were added. Additional 1.4 L of 100 mM phosphate buffer, pH 7.8 containing 10 mM EDTA was added to the reaction mixture. The reaction was started by the addition of 100 mL of cell-extracts of transaminase [aminotransferase (1 unit/mL activity) from *Escherichia coli*]. The pH was maintained at 7.8 with the addition of 5N NaOH. Periodically samples of 1 mL were removed and quenched with 0.1 mL of trichloroacetic acid and 0.9 mL of acetonitrile. The sample was allowed to stand at room temperature for 2 h, then filtered and analyzed by HPLC to measure the amount of [4S-(4α,7α,10aβ)]1-Octahydro-5-oxo-4-[(phenylmethoxy) carbonyl]amino]-7H-phrido-[2,1-b][1,3]thiazepine-7-carboxylic acid, methyl ester formed. After 6 hours of reaction time, 0.6 L of TCA solution (100% v/v) was added to the reactor to terminate the enzymatic reaction. The solution was mixed for 15 minutes, and let stand at room temperature for 3 hours. To the reaction, 5 L of acetonitrile was added and the amount of product formed was then obtained by an HPLC quantiation of an aliquot.

Yields

| Compound A. Substrate # | Input (g) | Compound A (g) | Compound B (g) | Compound B Yield (M %) |
|---|---|---|---|---|
| | 22.2 | 4.9 | 17.2 | 73 |

Evaluation of Different Compounds as Substrate for Transaminase

Two new dipeptides N-[N-[(Phenylmethoxy)carbonyl]-L-methionyl]-L-lysine (9) and N<2-[S-Acetyl-N-[(phenylmethoxy)carbonyl]-L-homocysteinyl]-L-lysine (10) were evaluated as substrates for dipeptide aminotransferase by cell-free extracts of *Spongomonas paucimobilis* ATCC 202027 in the presence of α-ketoglutarate. Glutamate oxidase was not used. As no product markers were available, the formation of new compounds from the enzymatic reaction were investigated by LC-MS. In case of (9) the data indicates the formation of a new compound with mol wt. of 392, the compound was assigned the tentative structure 1. The ε-NH₂ group of (9) was oxidized and in the presence of TCA the aldehyde cyclized to the enamide with loss of water.

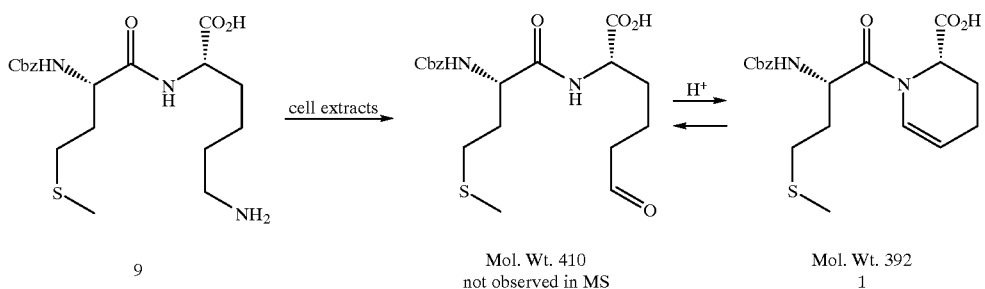

Mol. Wt. 410
not observed in MS

Mol. Wt. 392
1

9

When (10) was treated with cell-free extracts and α-ketoglutarate, several new components were observed by LC-MS. The component with mol wt. 420.5 was assigned structure 2, formed by the oxidation of the ε-NH₂ group of (3) N<2-[S-Acetyl-N-[(phenylmethoxy)carbonyl]-L-homocysteinyl]-L-lysine and subsequent dehydration to produce the cyclic enamide, the component with mol wt. 397 was proposed as Des-acetyl (3) N<2-[S-Acetyl-N-[(phenylmethoxy)carbonyl]-L-homocysteinyl]-L-lysine. The Des-acetyl (3) N<2-[S-Acetyl-N-[(phenylmethoxy)carbonyl]-L-homocysteinyl]-L-lysine and was then oxidized by the enzyme to [4S-(4α,7α,10aβ)]1-Octahydro-5-oxo-4-[(phenylmethoxy)carbonyl]amino]-7H-pyrido-[2,1-b][1,3]thiazepine-7-carboxylic acid, mol wt. of 378, as shown in the scheme below.

Reaction Conditions

The substrate 5, (conc. 5 mg/mL), namely the phenylacetyl analog, was incubated with recombinant transaminase in phosphate buffer, pH 8 containing 5 mM DTT, 1 mM Pyridoxal phosphate. The reaction was carried out in the absence of glutamate oxidase with 40 mg/mL α-ketoglutarate at 38° C. After 4H, the reaction was terminated with 10% TCA and 90% Acetonitrile. The product was identified as (6) [4S-4R*,7R*,10aR*)]-2,3,4,5,8,9,10,10a-Octahydro-4-[(phenylacetyl)amino]-7H-pyrido-[2,1-b][1,3]thiazepine-7-carboxylic acid, with a yield of 70%.

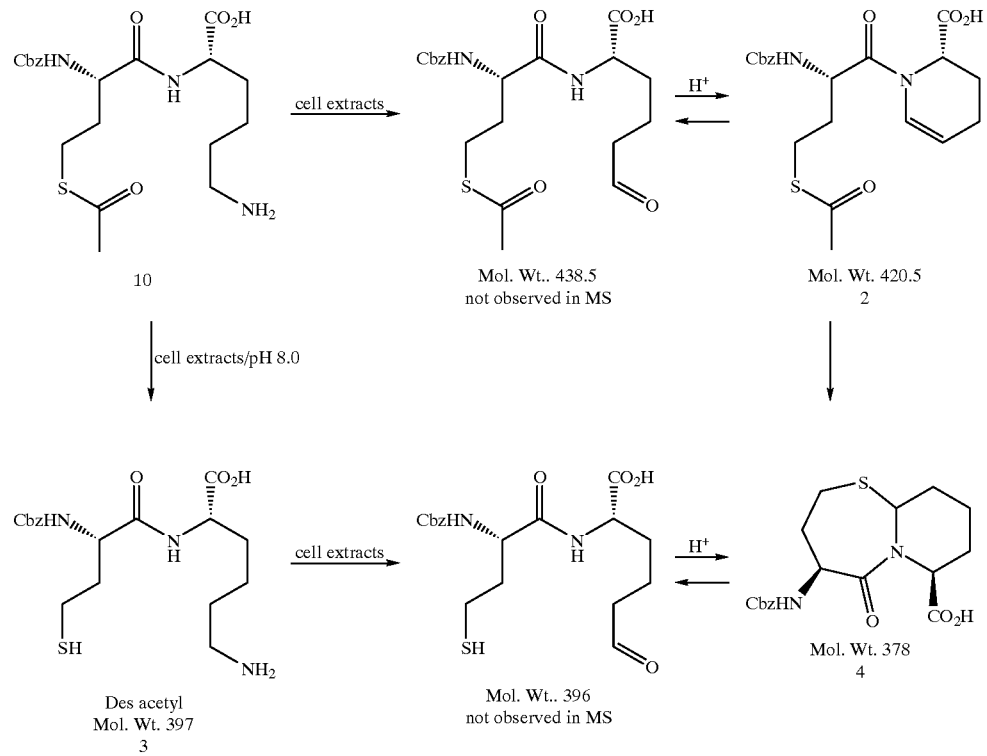

(3) Evaluation of N-Phenylacetyl Analog (4) as a Substrate for Transaminase (4) Evaluation of N-Phenoxyacetyl Analog (7) as a Substrate for Transaminase

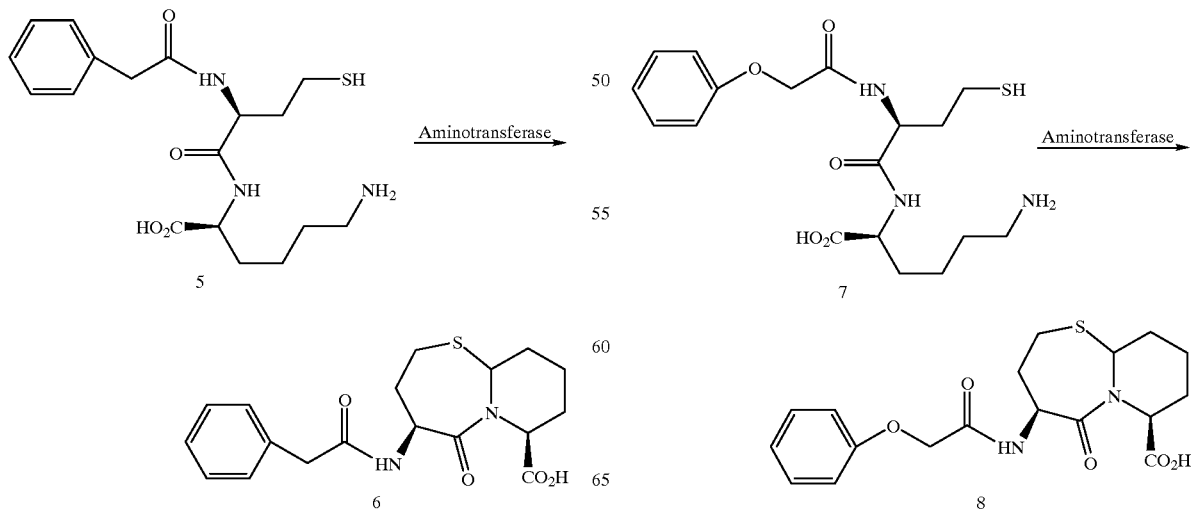

The substrate, $N^2$-[N-[(Phenoxyacetyl)carbonyl]-L-homocysteinyl]-L-lysine, (1->1')-disulfide, compound 7, which is an analog of $N^2$-[N-[(Phenylmethoxy)carbonyl]-L-homocysteinyl]-L-lysine, (1->1')-disulfide (Phenoxyacetyl was used in place of Cbz) was incubated with recombinant transaminase in the presence of DTT and α-ketoglutarate (the amino acceptor). After 6 hours of incubation, a new peak at 17.03 min. was observed. The new peak was identified as the product 8, [4S-(4R*,7R*,10aR*)]-2,3,4,5,8,9,10,10a-Octahydro-4-[(phenylacetyl)amino]-7H-pyrido-[2,1-b][1,3]thiazepine-7-carboxylic acid and based on the mass spec analysis and later conformed with an authentic standard.

Single Enzyme Process

To reduce the cost of producing two enzymes, the transamination reactions were carried out in the absence of glutamate oxidase and higher levels of α-ketogultarate. Historically, the reaction yield in the absence of glutamate oxidase averaged 33 M %. At 40 mg/mL of α-keto-glutarate (a 10× increase in concentration in the absence of glutamate oxidase in reaction mixture), at 40° C., the reaction yield increased to 70 M %.

Replacement of DTT

We have discovered that DTT can be used to cleave the disulfide bond of $N^2$-[N-[(Phenylmethoxy)carbonyl]-L-homocysteinyl]-L-lysine, (1->1')-disulfide to produce the dipeptide monomer, which is the substrate for the tranaminase. It was observed, that tributylphosphine was as effective as DTT for the dipeptide dimer to monomer conversion. In the presence of 10 mM tri-n-butylphosphine, 3.5 mg/mL of $N^2$-[N-[(Phenylmethoxy)carbonyl]-L-homocysteinyl]-L-lysine, (1->1')-disulfide, 40 mg/mL α-ketoglutarate and 0.1 units of transaminase, 69 M % [[4S-(4α,7α,10aβ)]1-Octahydro-5-oxo-4-[(phenylmethoxy)carbonyl]amino]-7H-pyrido-[2,1-b][1,3]thiazepine-7-carboxylic acid, was obtained.

3. Reduction of TCA

To terminate the transaminase reaction, 10% v/v TCA was used. After some optimization studies, the amount of TCA required to terminate the reaction was reduced to 5% v/v without loss in yields of [4S-(4α,7α,10aβ)]1-Octahydro-5-oxo-4-[(phenylmethoxy)carbonyl]amino]-7H-pyrido-[2,1-b][1,3]thiazepine-7-carboxylic acid. It was also observed that methane sulfonic acid or sulfuric acid, or hydrochloric acid or acetic acid or phosphoric acid can be used in place of TCA.

What is claimed is:

1. An isolated DNA sequence encoding the aminotransferase of SEQ ID NO: 2, or the complement thereof.

2. An isolated DNA sequence encoding an amino transferase having at least 80% identity to SEQ ID NO: 2, or the complement thereof.

3. An isolated DNA sequence having the sequence of SEQ ID NO: 1 or its complement.

4. An isolated DNA sequence capable of hybridizing under stringent conditions to a sequence of claim 3, wherein said isolated DNA sequence encodes an aminotransferase or a fragment of an aminotransferase that is catalytically active, and wherein said stringent conditions are: incubation in 4×SET buffer, 10×Denhardt's solution, 0.1% SDS, 0.1% sodium pyrophosphate, 50 µg/ml denatured salmon sperm DNA at 68° C. for 16–24 hours; followed by washing three times for 20 minutes in 3×SET, 0.1% SDS, 0.1% sodium pyrophosphate at 68° C., washing twice for 20 minutes in 1×SET, 0.1% SDS, 0.1% sodium pyrophosphate at 68° C., washing once for 20 minutes in 0.1×SET, 0.1% SDS, 0.1% sodium pyrophosphate at 68° C., and washing once for 20 minutes in 4×SET at room temperature.

5. An isolated DNA sequence selected from the group consisting of: (a) an isolated DNA sequence encoding a fragment of the amino acid sequence of SEQ ID NO: 2 that is catalytically active, or the complement thereof; and (b) an isolated DNA sequence capable of hybridizing under stringent conditions to the sequence encoding a fragment of the amino acid sequence of SEQ ID NO: 2 that is catalytically active, or the complement thereof, wherein said isolated DNA sequence capable of hybridizing encodes an aminotransferase or a fragment of an aminotransferase that is catalytically active, and wherein said stringent conditions are: incubation in 4×SET buffer, 10×Denherdt's solution, 0.1% SDS, 0.1% sodium pyrophosphate, 50 µg/ml denatured salmon sperm DNA at 68° C. for 16–24 hours; followed by washing three times for 20 minutes in 3×SET, 0.1% SDS, 0.1% sodium pyrophosphate at 68° C., washing twice for 20 minutes in 1×SET, 0.1% SDS, 0.1% sodium pyrophosphate at 68° C., washing once for 20 minutes in 0.1×SET, 0.1% SDS, 0.1% sodium pyrophosphate at 68° C., and washing once for 20 minutes in 4×SET at room temperature.

6. An isolated DNA sequence consisting of the sequence of SEQ ID NO:3 or its complement.

7. A vector comprising the nucleic acid molecule of claim 1.

8. A vector comprising the nucleic acid molecule of claim 3.

9. A vector comprising the nucleic acid molecule of claim 4.

10. A vector comprising the nucleic acid molecule of claim 5.

11. A vector comprising the nucleic acid molecule of claim 6.

12. The vector of claim 7, wherein the nucleic acid molecule is operatively linked to one or more regulatory DNA sequences.

13. The vector of claim 8, wherein the nucleic acid molecule is operatively linked to one or more regulatory DNA sequences.

14. The vector of claim 9, wherein the nucleic acid molecule is operatively linked to one or more regulatory DNA sequences.

15. A method of producing a host cell comprising genetically engineering cells with the vector of claim 7.

16. A method of producing a host cell comprising genetically engineering cells with the vector of claim 8.

17. A method of producing a host cell comprising genetically engineering cells with the vector of claim 9.

18. A host cell comprising the vector of claim 7.

19. A host cell comprising the vector of claim 8.

20. A host cell comprising the vector of claim 9.

21. The host cell of claim 18 wherein said host cell is prokaryotic or eukaryotic.

22. The host cell of claim 19 wherein said host cell is prokaryotic or eukaryotic.

23. The host cell of claim 20 wherein said host cell is prokaryotic or eukaryotic.

24. The host cell of claim 21 which is *E. coli*.

25. The host cell of claim 22 which is *E. coli*.

26. The host cell of claim 23 wherein said host cell is prokaryotic or eukaryotic.

27. A method of producing an aminotransferase comprising culturing a host cell of claim 18 under conditions permitting expression of said aminotransferase.

28. A method of producing an aminotranferase comprising culturing a host cell of claim 19 under conditions permitting expression of said aminotransferase.

29. A method of producing an aminotransferase comprising culturing a host cell of claim 20 under conditions permitting expression of said aminotransferase.

* * * * *

UNITED STATES PATENT AND TRADEMARK OFFICE
CERTIFICATE OF CORRECTION

PATENT NO. : 6,649,387 B2
DATED : November 18, 2003
INVENTOR(S) : Patel et al.

It is certified that error appears in the above-identified patent and that said Letters Patent is hereby corrected as shown below:

Column 30,
Line 8, "pkk 223-3-LAT" should read -- pKK223-3-LAT --
Line 16, "OD600" should read -- $OD_{600}$ --
Lines 33 and 35, "Tg/ml" should read -- µg/ml --.
Line 17, "100 TM" should read -- 100 µM --
Lines 28 and 32, "MgSO4" should read -- $MgSO_4$ --
Line 66, "$Kn^R$" should read -- $Km^R$ --

Signed and Sealed this

Twenty-ninth Day of June, 2004

JON W. DUDAS
*Acting Director of the United States Patent and Trademark Office*